(12) United States Patent
Arthur et al.

(10) Patent No.: US 12,121,115 B2
(45) Date of Patent: Oct. 22, 2024

(54) SELF-MATING MECHANICAL FASTENER WITH CONDUCTIVE CONTACT ELEMENT

(71) Applicant: 3M INNOVATIVE PROPERTIES COMPANY, St. Paul, MN (US)

(72) Inventors: Cory M. Arthur, Eagan, MN (US); David T. Buckley, Falcon Heights, MN (US); Dylan T. Cosgrove, Oakdale, MN (US); Kurt J. Halverson, Lake Elmo, MN (US); Karl M. Kropp, St. Paul, MN (US); Audrey A. Sherman, Woodbury, MN (US); Steven P. Swanson, Blaine, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 448 days.

(21) Appl. No.: 17/598,026

(22) PCT Filed: Apr. 7, 2020

(86) PCT No.: PCT/IB2020/053310
§ 371 (c)(1),
(2) Date: Sep. 24, 2021

(87) PCT Pub. No.: WO2020/208522
PCT Pub. Date: Oct. 15, 2020

(65) Prior Publication Data
US 2022/0175094 A1    Jun. 9, 2022

Related U.S. Application Data

(60) Provisional application No. 62/831,970, filed on Apr. 10, 2019.

(51) Int. Cl.
A44B 18/00     (2006.01)
A61B 5/00      (2006.01)
A61M 25/02     (2006.01)

(52) U.S. Cl.
CPC .......... *A44B 18/0053* (2013.01); *A61B 5/683* (2013.01); *A61M 25/02* (2013.01)

(58) Field of Classification Search
CPC ..... A44B 18/0053; A61B 5/683; A61B 5/021; A61B 5/024; A61B 5/026; A61B 5/08;
(Continued)

(56) References Cited

U.S. PATENT DOCUMENTS 3,408,705 A   11/1968  Kayser
4,775,310 A   10/1988  Fischer
(Continued)

FOREIGN PATENT DOCUMENTS

EP   2175704    4/2010
GB   2152870    3/1987
(Continued)

OTHER PUBLICATIONS

International Search Report for PCT International Application No. PCT/IB2020/053310, mailed on Jul. 23, 2020, 3 pages.

*Primary Examiner* — David M Upchurch

(57) ABSTRACT

Aspects of the present disclosure relate to a self-mating fastener that includes a backing having a first side, and a rail element protruding perpendicularly from the first side of the backing. The rail element extends in a longitudinal direction along the backing. The rail element has a base portion attached to the first side of the backing and a cap portion distal from the backing. The cap portion has a cap width that is greater than a width of the base portion and the cap portion overhangs the base portion on opposing sides. The self-mating fastener includes an electrically conductive contact element proximate to the rail element.

21 Claims, 13 Drawing Sheets

(58) Field of Classification Search
CPC ..... A61B 5/14532; A61B 5/318; A61B 5/441; A61M 25/02; F16B 5/07; F16B 2200/93
See application file for complete search history.

(56) References Cited

U.S. PATENT DOCUMENTS

| | | | |
|---|---|---|---|
| 4,894,060 A | 1/1990 | Nestegard | |
| 5,040,275 A | 8/1991 | Eckhardt | |
| 5,067,210 A * | 11/1991 | Keyaki | B29C 45/44 24/442 |
| 5,071,263 A | 12/1991 | Kamiya | |
| 5,071,363 A | 12/1991 | Reylek | |
| 5,077,870 A | 1/1992 | Melbye | |
| 5,113,555 A | 5/1992 | Wilson | |
| 5,212,853 A * | 5/1993 | Kaneko | A44B 18/0053 24/442 |
| 5,235,731 A * | 8/1993 | Anzai | A44B 18/0053 24/DIG. 39 |
| 5,312,456 A | 5/1994 | Reed | |
| 5,586,372 A * | 12/1996 | Eguchi | A44B 18/0053 24/442 |
| 5,685,050 A * | 11/1997 | Murasaki | A44B 18/0061 24/442 |
| 5,884,374 A | 3/1999 | Clune | |
| 5,945,193 A | 8/1999 | Pollard | |
| 6,000,106 A | 12/1999 | Kampfer | |
| 6,061,881 A * | 5/2000 | Takizawa | A44B 18/0061 24/446 |
| 6,106,922 A | 8/2000 | Cejka | |
| 6,132,660 A | 10/2000 | Kampfer | |
| 6,190,594 B1 | 2/2001 | Gorman | |
| 6,276,032 B1 * | 8/2001 | Nortman | A61F 13/622 24/572.1 |
| 6,287,665 B1 | 9/2001 | Hammer | |
| 6,367,128 B1 | 4/2002 | Galkiewicz | |
| 6,546,604 B2 * | 4/2003 | Galkiewicz | A44B 18/0092 24/584.1 |
| 6,588,074 B2 | 7/2003 | Galkiewicz | |
| 6,592,800 B1 | 7/2003 | Levitt | |
| 6,627,133 B1 | 9/2003 | Tuma | |
| 6,919,504 B2 | 7/2005 | Mccutcheon | |
| 7,140,774 B2 | 11/2006 | Galkiewicz | |
| 7,185,401 B2 | 3/2007 | Ausen | |
| 7,195,729 B2 | 3/2007 | Jackson | |
| 7,198,743 B2 | 4/2007 | Tuma | |
| 7,214,334 B2 | 5/2007 | Jens | |
| 7,709,749 B2 | 5/2010 | Meier | |
| 7,850,740 B2 | 12/2010 | Cox | |
| 7,897,078 B2 | 3/2011 | Petersen | |
| 8,758,237 B2 | 6/2014 | Sherman | |
| 8,877,125 B2 | 11/2014 | Appeaning | |
| 9,015,910 B2 * | 4/2015 | Septien Rojas | A44B 19/16 24/399 |
| 9,480,760 B2 | 11/2016 | Appeaning | |
| 9,687,048 B2 | 6/2017 | Gilbert | |
| 10,334,723 B2 * | 6/2019 | Wald | H05K 1/0281 |
| 11,116,090 B2 * | 9/2021 | Cosgrove | A44B 18/0046 |
| 2001/0013277 A1 * | 8/2001 | Galkiewicz | A44B 18/0092 100/2 |
| 2001/0018785 A1 | 9/2001 | Galkiewicz | |
| 2002/0170806 A1 * | 11/2002 | Engle | F16G 3/00 198/844.2 |
| 2003/0051320 A1 * | 3/2003 | Fagan | A44B 18/0084 24/584.1 |
| 2004/0117955 A1 | 6/2004 | Barvosa-Carter | |
| 2008/0035173 A1 | 2/2008 | Tuman | |
| 2009/0010735 A1 * | 1/2009 | Gallant | A44B 18/0053 411/510 |
| 2011/0265292 A1 * | 11/2011 | Kirby | F16M 13/022 24/442 |
| 2014/0199904 A1 | 7/2014 | Creasy | |
| 2017/0066181 A1 | 3/2017 | Poulakis | |
| 2017/0066225 A1 | 3/2017 | Chen | |
| 2018/0147766 A1 | 5/2018 | Sura | |

FOREIGN PATENT DOCUMENTS

| | | |
|---|---|---|
| JP | S57-176132 | 10/1982 |
| WO | WO 2016-196180 | 12/2016 |
| WO | WO 2016-196736 | 12/2016 |
| WO | WO 2018-102215 | 6/2018 |
| WO | WO 2019-018251 | 1/2019 |
| WO | WO 2019-018253 | 1/2019 |
| WO | WO 2019-102430 | 5/2019 |
| WO | WO 2019-102431 | 5/2019 |
| WO | WO 2019-102432 | 5/2019 |
| WO | WO 2020-141477 | 7/2020 |

* cited by examiner

SELF-MATING MECHANICAL FASTENER WITH CONDUCTIVE CONTACT ELEMENT

CROSS REFERENCE TO RELATED APPLICATIONS

This application is a national stage filing under 35 U.S.C. 371 of PCT/IB2020/053310, filed 7 Apr. 2020, which claims the benefit of U.S. Provisional Patent Application No. 62/831,970, filed 10 Apr. 2019, the disclosure of which is incorporated by reference in its/their entirety herein.

BACKGROUND

Fasteners are used in a variety of applications, including construction, machinery, medical equipment, automobile assembly, personal care products, and the textile industry. Commonly known fasteners range from rivets, snaps and buttons to hook and loop fasteners, each of which involve joining unlike components (e.g., male and female components) for assembling two articles together. Some fasteners, which are sometimes called self-mating fasteners or hook-and-hook fasteners, are composed of interlocking members that do not include male and female components. For assembling two articles together, each fastening member is attached to a surface of its respective article, and the two articles are joined together when the fastening members are mated.

Certain fasteners have been reported that include different structures on the same fastening member. See, for example, U.S. Pat. No. 5,586,372 (Eguchi); U.S. Pat. No. 5,884,374 (Clune); U.S. Pat. No. 6,276,032 (Nortman); and U.S. Pat. No. 6,546,604 (Galkiewicz). The different structures may have different shapes, sizes, or abilities to engage.

Some mechanical fasteners with conductive elements have been reported. See, for example, U.S. Pat. No. 7,850,740 (Ales), or U.S. Pat. No. 7,709,749 (Meier). However, none of the existing solutions have called for a self-mating fastener. Further, these designs are not conducive to being slidable while maintaining an electrical connection.

SUMMARY

Aspects of the present disclosure relate to a self-mating fastener that includes a backing having a first side, and a rail element protruding perpendicularly from the first side of the backing. The rail element extends in a longitudinal direction along the backing. The rail element has a base portion attached to the first side of the backing and a cap portion distal from the backing. The cap portion has a cap width that is greater than a width of the base portion and the cap portion overhangs the base portion on opposing sides. The self-mating fastener includes an electrically conductive contact element proximate to the rail element.

When used as a system, at least two self-mating fasteners can be slidable relative to each other while maintaining an electrical connection. Additionally, electronic devices can be electrically coupled to the self-mating fastener to facilitate communication from a first electronic device to a second electronic device.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

Aspects of the present disclosure relate to a self-mating fastener having electrically conductive contact elements. Additional aspects of the present disclosure also relate to a system of self-mating fasteners arranged such that a first self-mating fastener is slidable with respect to a second self-mating fastener while maintaining an electrical connection.

Figure 1A:
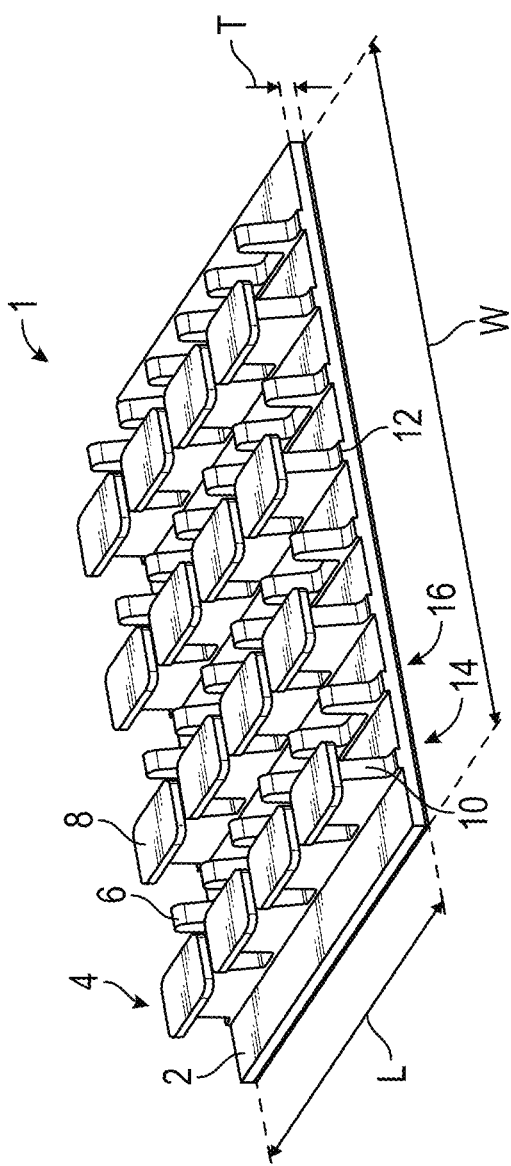
FIG. 1A is a schematic perspective view of an embodiment of a fastener of the present disclosure.
Figure 1B:
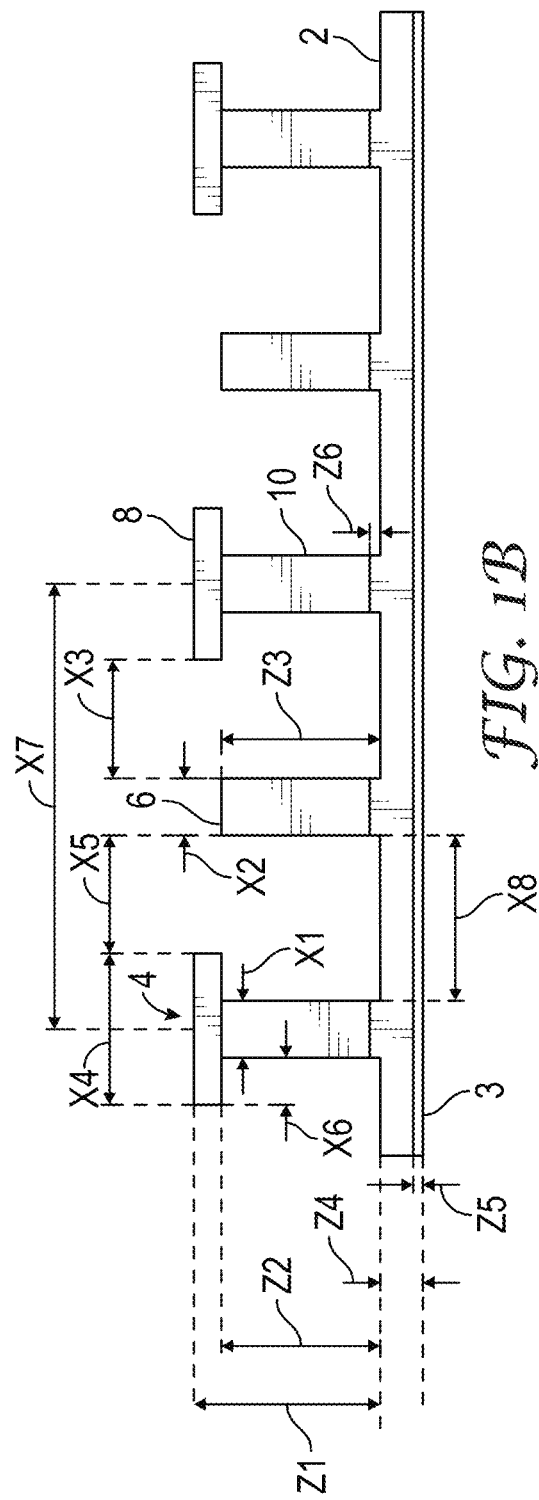
FIG. 1B is a schematic side view of the fastener of FIG. 1A.
Figure 1C:
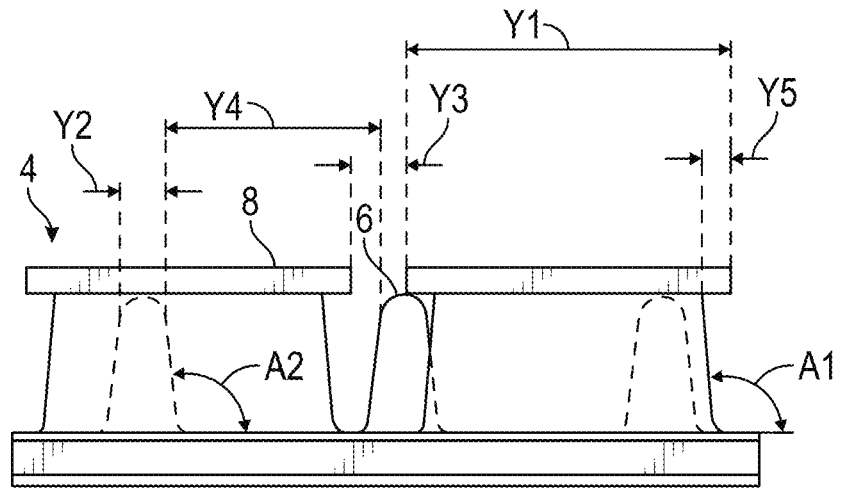
FIG. 1C is a schematic side view of the fastener of FIG. 1A, which side view is orthogonal to the side view shown in FIG. 1B.

An embodiment of a fastener of the present disclosure is shown in FIGS. 1A, 1B, and 1C. Fastener 1 includes a backing 2 having a length (l), a width (w), and a thickness (t). Fastener 1 includes rows 14 of rail segments 4. In the embodiment illustrated in FIGS. 1A, 1B, and 1C, the rail segments 4 protrude perpendicularly from the backing 2. Each of the rail segments 4 has a base portion 10 attached to the backing 2 and a cap portion 8 distal from the backing 2. The cap portion 8 has a cap width X4 that is greater than the width X1 of the base portion 10, and the cap portion 8 overhangs the base portion 10 on opposing sides. The ratio of the cap width X4 to the width X1 of the base portion 10 is typically at least 1.25:1, 1.5:1, or 2:1 and can be up to 3:1, 4:1, or 5:1. FIG. 1B illustrates the cap overhang distance X6. In some embodiments, the cap portion 8 overhangs the base portion 10 on all sides of base portion 10. FIG. 1C illustrates the cap overhang distance Y5, in the direction parallel to the length (l) of the fastener 1. Caps also have a cap thickness, which, if the cap is not rectilinear, is measured as a distance between a line tangent to the highest point on the cap above the backing and a line tangent to lowest point on the cap above the backing. For example, in the embodiment shown in FIG. 1B, the cap thickness is Z1 minus Z2. From the term "rows of rail segments", it should be understood that each row 14 includes more than one rail segment 4. The fastener 1 does not include a continuous rail; instead the rail segments 4 are separated from each other on the backing 2. For example, the caps 8 of the rail segments 4 in a row 14 are separated by cap-to-cap distance Y3 in the direction parallel to the length (l) of the fastener 1.

The base portion 10 of the rail segment 4 has a length Y1 that is greater than the width X1 of the base portion 10. In some embodiments, the ratio of the length Y1 to the width X1 of the base portion 10 is at least about 1.5:1, 2:1, 3:1, 4:1, or 5:1, 10:1, or 15:1. The base portion 10 of the rail segment 4 may have a variety of cross-section shapes. For example, the cross-sectional shape of the base portion 10 may be a polygon (e.g., rectangle, hexagon, or octagon), or the cross-sectional shape of the base portion 10 may be curved (e.g., elliptical). The base portion 10 may taper from its base to its distal end. In this case and in the case of curved base portions, the ratio of the length Y1 to the width X1 of the base portion 10 is measured from the longest and the widest point. As shown in FIG. 1B the length Y1 of the base portion at its longest point is about the same as the length of the cap portion.

For embodiments such as the embodiment illustrated in FIG. 1C, base portions 10 that taper from their bases to their distal ends have a sloping face and a taper angle A1 between the sloping face and the backing 2. In some embodiments, the taper angle A1 between the sloping face of the base portion 10 and the backing 2 is in a range from 91 degrees to 130 degrees, in some embodiments, in a range from 91 degrees to 125 degrees, 95 degrees to 120 degrees, 95 degrees to 115 degrees, 95 degrees to 110 degrees, 93 degrees to 105 degrees, or 95 degrees to 100 degrees.

In some embodiments, the rail segments 4 have a maximum height Z1 (above the backing 2) of up to 3 millimeter (mm), 1.5 mm, or 1 mm and, in some embodiments, a minimum height of at least 0.1 mm or 0.2 mm. The height Z1 of the rail segments 4 can be in a range from 0.3 mm to 0.7 mm, 0.3 mm to 0.6 mm, or 0.35 mm to 0.55 mm. The thickness of the cap portion 8 (e.g., Z1-Z2) of rail segments 4 can be in a range from 0.03 mm to 0.3 mm, 0.04 mm to 0.15 mm, or 0.04 mm to 0.1 mm. In some embodiments, the base portions 10 of the rail segments 4 have a maximum width X1 of up to about 0.5 mm, 0.4 mm, 0.3 mm, or 0.2 mm and a minimum width of at least 0.05 mm, 0.1 mm, or 0.125 mm. Some useful widths X1 of the base portions 10 are in a range from 0.05 mm to 0.5 mm, 0.1 mm to 0.2 mm, or 0.125 mm to 0.175 mm. Some useful cap widths X4 of the rail segments 4 are in a range from 0.1 mm to 1.0 mm, 0.3 mm to 0.5 mm, 0.3 mm to 0.45 mm, or 0.3 mm to 0.4 mm. Some useful cap overhang distances X6 of the rail segments 4 are in a range from 0.025 mm to 0.4 mm, 0.05 mm to 0.3 mm, or 0.1 m to 0.25 mm. In some embodiments, the rail segments 4 have a maximum length Y1 of up to about 1.5 mm (in some embodiments, up to 1.25, 1.0, 0.9, or 0.8) mm and a minimum length Y1 of at least about 0.1 mm, 0.2 mm, 0.4 mm, or 0.5 mm. The length Y1 of the rail segments can be in a range from 0.1 mm to 1.5 mm, 0.2 mm to 1.0 mm, or 0.600 mm to 0.800 mm. Some useful cap overhang distances Y5 of the rail segments 4 in the length direction are in a range from 0.025 mm to 0.2 mm, 0.025 mm to 0.1 mm, or 0.04 mm to 0.075 mm. In some embodiments, the cap-to-cap distance Y3 in the direction parallel to the length (l) of the fastener 1 is up to about 0.5 mm, 0.4 mm, 0.3 mm, or 0.25 mm and at least about 0.05 mm, 0.1 mm, or 0.125 mm. Some useful cap-to-cap distances Y3 are in a range from 0.05 mm to 0.5 mm, 0.1 mm to 0.3 mm, or 0.125 mm to 0.225 mm.

The fastener of the present disclosure typically also comprises rows of posts. In the embodiment illustrated in FIGS. 1A, 1B, and 1C, the fastener 1 includes rows 16 of posts 6 protruding perpendicularly from the backing 2. In some embodiments, the rows 14 of rail segments 4 and rows 16 of posts 6 alternate. The fastener 1 can have at least 2, 3, 5, or 10 of the rows 14 of rail segments 4 alternating with at least 2, 3, 5, or 10 of the rows 16 of posts 6. From the term "rows of posts", it should be understood that each row 16 includes more than one post 6. The fastener 1 does not include a continuous ridge; instead the posts 6 are separated from each other on the backing 2. For example, the posts 6 in a row 16 are separated by a distance Y4 in the direction parallel to the length (l) of the fastener 1. In general, the posts have a length that is different from the length of the rail segments. In the embodiment illustrated in FIGS. 1A, 1B, and 1C, the length Y1 of the base portion 10 of the rail segments 4 is greater than the length Y2 of the post 6, and the number of posts 6 in one of the rows 16 of posts is more than the number of rail segments 4 in one of the rows of rail segments 14. The length Y1 of the base portion 10 of the rail segments 4 can be at least two, three, or four times the length Y2 of the posts 6. The number of posts 6 in one of the rows 16 of posts can be at least 1.5, 2, or 3 times the number of rail segments 4 in one of the rows of rail segments 14. Since the fastener 1 is useful as a self-mating fastener, the posts generally have a height that is no greater than a height of the rail segments. In the embodiment illustrated in FIGS. 1A, 1B, and 1C, the height Z3 of the posts 6 is less than the height Z1 of the rail segments 4. In some embodiments, the height Z3 of posts 6 is up to 95, 90, 80, 75, or 70 percent of the height Z1 of the rail segments 4.

Posts useful in the fastener of the present disclosure may have a variety of cross-sectional shapes in a plane parallel to the backing. For example, the cross-sectional shape of the post may be a polygon (e.g., square, rectangle, rhombus, hexagon, pentagon, or dodecagon), which may be a regular polygon or not, or the cross-sectional shape of the post may be curved (e.g., round or elliptical). In some embodiments, the post has a base attached to the backing and a distal end, and the distal end has a cross-sectional area that is less than or equal to a cross-sectional area of the base. The post may taper from its base to its distal end, but this is not a requirement. In some embodiments, the post has a distal cap with a cap width that is greater than the width of the base. The cap can overhang the base on opposing sides or may overhang the base on all sides. Capped posts useful in the fastener of the present disclosure can have a variety of useful shapes including a mushroom (e.g., with a circular or oval head enlarged with respect to the stem), a nail, a T, or a golf tee.

Referring again to FIGS. 1A, 1B, and 1C, in some embodiments, posts 6 useful in the fastener of the present disclosure have a maximum width X2 of up to about 0.5 mm, 0.4 mm, 0.3 mm, or 0.2 mm and a minimum width of at least 0.05 mm, 0.1 mm, or 0.125 mm. Some useful widths X2 of the posts 6 are in a range from 0.05 mm to 0.5 mm, 0.1 mm to 0.2 mm, or 0.125 mm to 0.175 mm. In some embodiments, posts 6 useful in the fastener of the present disclosure have a maximum length Y2 of up to about 0.5 mm, 0.4 mm, 0.3 mm, or 0.2 mm and a minimum width of at least 0.05 mm, 0.1 mm, or 0.125 mm. Some useful widths Y2 of the post 6 are in a range from 0.05 mm to 0.5 mm, 0.1 mm to 0.2 mm, 0.1 mm to 0.15 mm, or 0.125 mm to 0.175 mm. In some embodiments, the distance Y4 between posts 6 in the direction parallel to the length (l) of the fastener 1 is up to about up to about 1.5 mm (in some embodiments, up to 1.25, 1.0, 0.9, or 0.8) mm and at least about 0.1 mm, 0.2 mm, or 0.4 mm. The distance Y4 between posts 6 can be in a range from 0.1 mm to 1.5 mm, 0.2 mm to 1.0 mm, or 0.400 mm to 0.600 mm.

For embodiments such as the embodiment illustrated in FIG. 1C, posts 6 that taper from their bases to their distal tips have a sloping face and a taper angle A2 between the sloping face and the backing 2. In some embodiments, the taper angle A2 between the sloping face of the post 6 and the backing 2 is in a range from 91 degrees to 130 degrees, in some embodiments, in a range from 91 degrees to 125 degrees, 91 degrees to 120 degrees, 91 degrees to 115 degrees, 91 degrees to 110 degrees, 91 degrees to 105 degrees, or 95 degrees to 100 degrees.

In some embodiments, the posts 6 have a maximum height Z3 (above the backing 2) of up to 2.85 millimeter (mm), 1.25 mm, or 1 mm and, in some embodiments, a minimum height of at least 0.08 mm or 0.16 mm. The height Z3 of the posts can be in a range from 0.2 mm to 0.6 mm, 0.3 mm to 0.6 mm, 0.3 mm to 0.4 mm, or 0.35 mm to 0.55 mm. In some embodiments, each of the posts has a height-to-width aspect ratio that is at least 1.5:1, at least 2:1, or at least 3:1. In some embodiments, each of the posts has a height-to-length aspect ratio that is at least 1.5:1, at least 2:1, or at least 3:1.

Figure 2A:
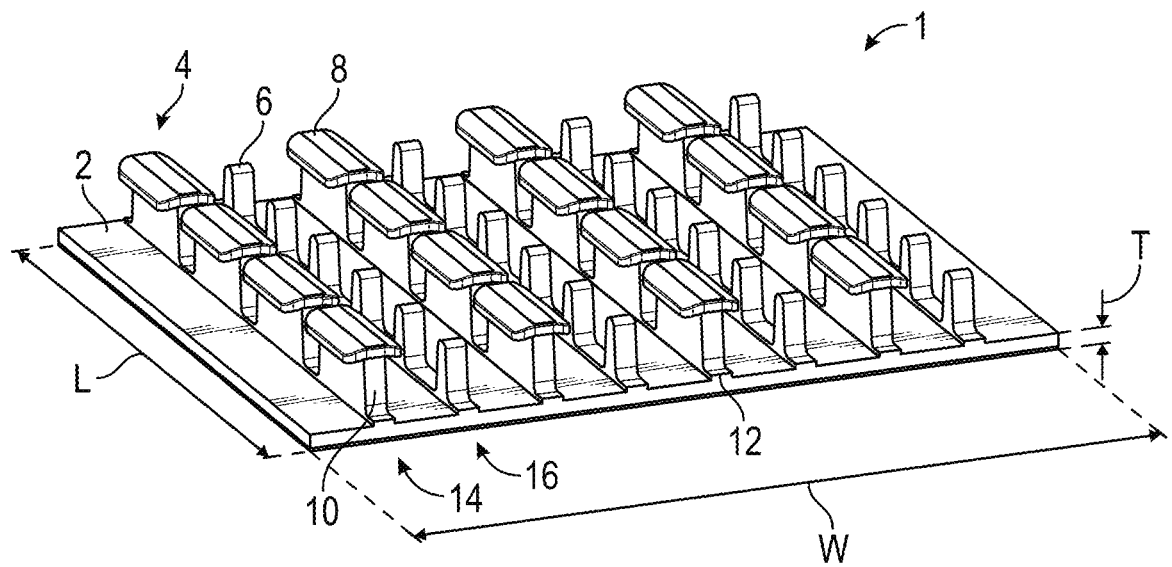
FIG. 2A is a schematic perspective view of another embodiment of a fastener of the present disclosure.
Figure 2B:
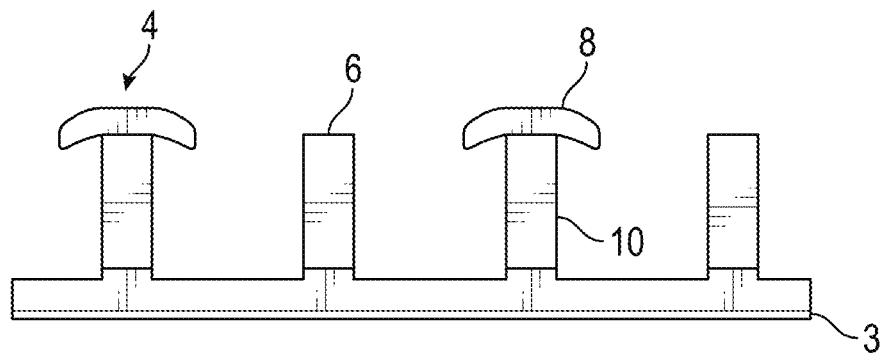
FIG. 2B is a schematic side view of the fastener of FIG. 2A.

Another embodiment of a fastener of the present disclosure is shown in FIGS. 2A and 2B. In this embodiment, the cap portion 8 of the rail segment 4 has a different shape than the cap portion 8 of the embodiment shown in FIGS. 1A, 1B, and 1C. The features and dimensions of any of the embodiments described above for the fastener shown in FIGS. 1A, 1B, and 1C can be used in combination with the fastener shown in FIGS. 2A and 2B to provide corresponding embodiments.

Figure 2C:
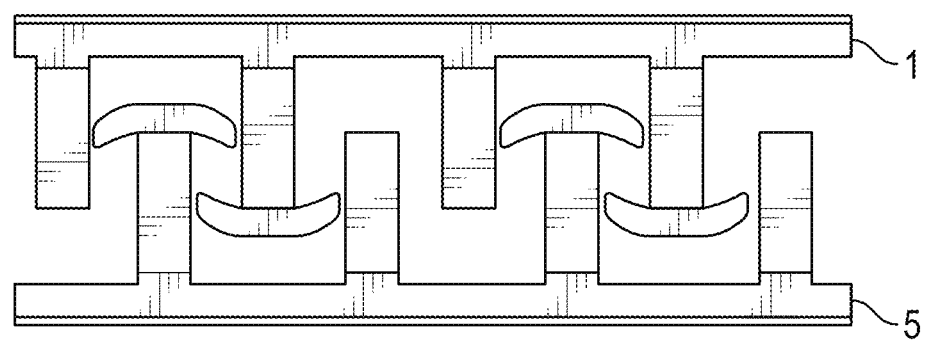
FIG. 2C is a schematic side view of an embodiment of a fastening system of the present disclosure in which both fastener members include the fastener of FIG. 2A and FIG. 2B.
Figure 3A:
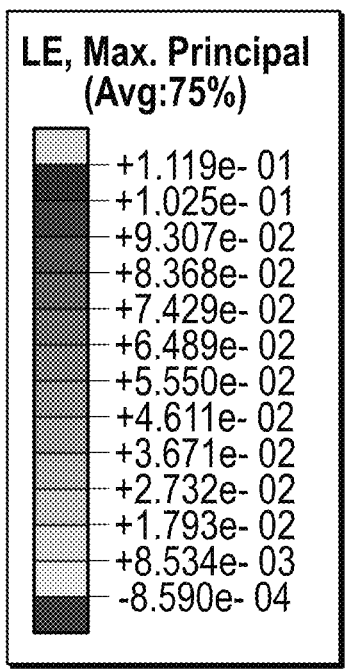
FIG. 3A is a schematic side view of an embodiment of fastener of the present disclosure undergoing deformation during fastening, with strain calculated by Finite Element Modeling depicted by shading.
Figure 3A:
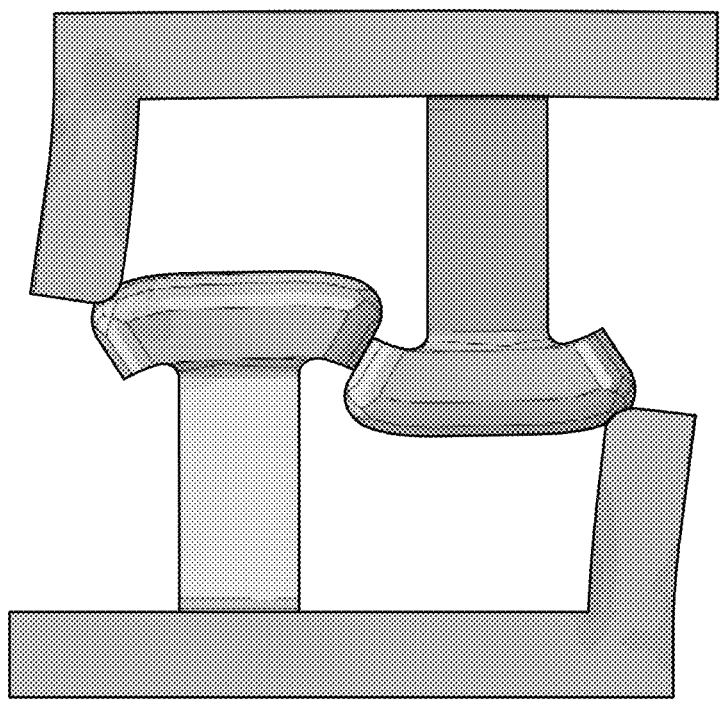
Figure 3B:
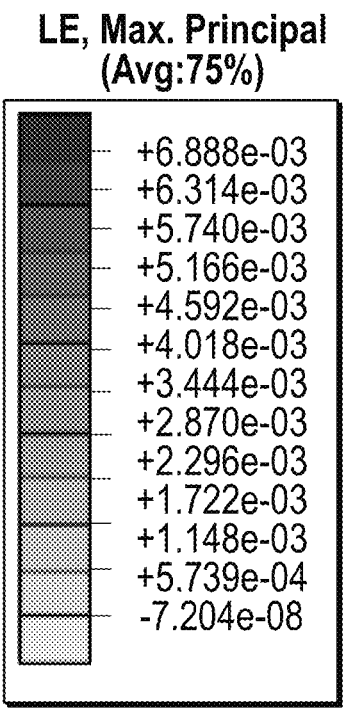
FIG. 3B is a schematic side view of the fastener of FIG. 3A after fastening, with residual strain calculated by Finite Element Modeling depicted by shading.
Figure 3B:
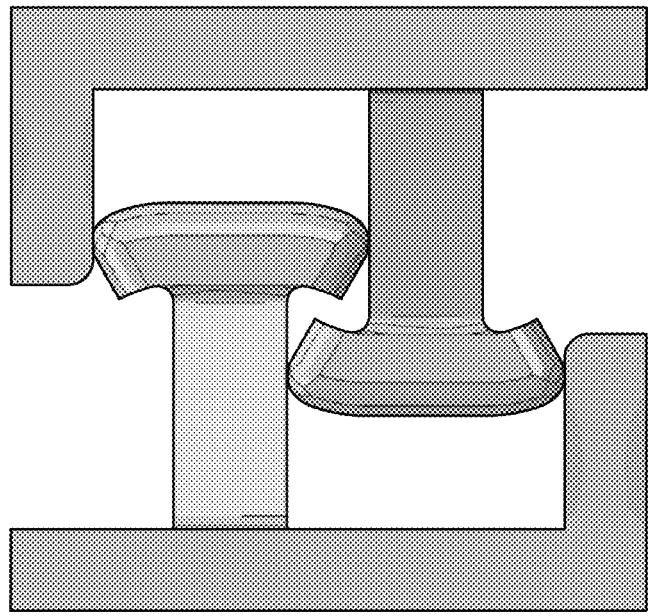

Fastener 1 is useful, for example, as a self-mating fastener. As used herein, self-mating refers to fasteners in which fastening is accomplished by interengaging fastening elements of the same type (e.g., fastening heads). In some embodiments, self-mating refers to fasteners in which fastening is accomplished by interengaging fastening elements of identical shape. In some embodiments, self-mating refers to the ability for the fastener to engage with itself when it is in a folded configuration, for example, along an axis parallel to either the length (L) or width (W) of the fastener, referring to FIGS. 1A and 2A. Two fastener members (e.g., first and second fastener members (1,5)), each having the structure shown in FIGS. 2A and 2B, for example, can be fastened together in a self-mating engagement as shown in FIG. 2C. In some embodiments, a first self-mating fastener 1 is a fastener of the present disclosure as described above in any of its embodiments, and a second self-mating fastener may include the rail segments but not include the posts. In some embodiments, the first and second fastener members may be different embodiments of the fastener of the present disclosure. For example, the first self-mating fastener 1 may have a cap shape like that shown in FIG. 1A and a second self-mating fastener 5 may have a cap shape like that shown in FIG. 2A. In any of these embodiments, when the first and second fastener members 1, 5 undergo fastening, the posts typically bend away from the rail segments while the cap portions of the rail segments of the first and second fastener members pass by each other as shown in FIG. 3A. The posts then return to their original positions after the first and second fastener members are fastened as shown in FIG. 3B.

In at least one embodiment, a featured side of the fastener (i.e., the side of the backing having posts and rails) can further have an electrically conductive contact element including an electrically conductive layer disposed on at least a portion thereon. In one example, the electrically conductive layer is disposed over the entire featured surface such that the entire first side is conductive. The electrically conductive layer can be any metalized particle or conductive polymer. Methods of forming the electrically conductive layer include sputtering, electrolytic coating, an electrically conductive material (such as copper or tin) onto the posts, rails, and areas in-between on the featured side. When two fasteners that are coated with an electrically conductive material are fastened, then an electrical pathway is formed on the featured side from one fastener to another fastener.

Accordingly, in some embodiments, the posts have a lower bending stiffness than that of the rail segments. The bending stiffness k for small strain behavior is determined by the equation $k=3EI/H$, in which E is the modulus of the material making up the posts and the rail segments, H is the height of the posts or rail segments, and $I=W^3L/12$, in which W is the width and L is the length of the posts or rail segments. In some embodiments, the length of the base portion of the rail segments is greater than a length of the posts. In these embodiments, when the width of the base portion and the width of the posts are similar, the bending stiffness of the rail segments will be higher than the bending stiffness of the posts. Referring again to FIG. 1A, the rows 14 of rail segments 4 can collectively have a higher bending stiffness than rows 16 of posts 6. When there are more posts 6 in a row 16 of posts, the bending stiffness of the posts can be adjusted (e.g., by selection length or width) so that collectively the row 16 of posts 6 has less bending stiffness than a row 14 of rail segments 4. The bending stiffness of each row of rail segments or posts can be determined by the number of rail segments or posts in each row and the bending stiffness of each of the rail segments or posts.

Figure 4:
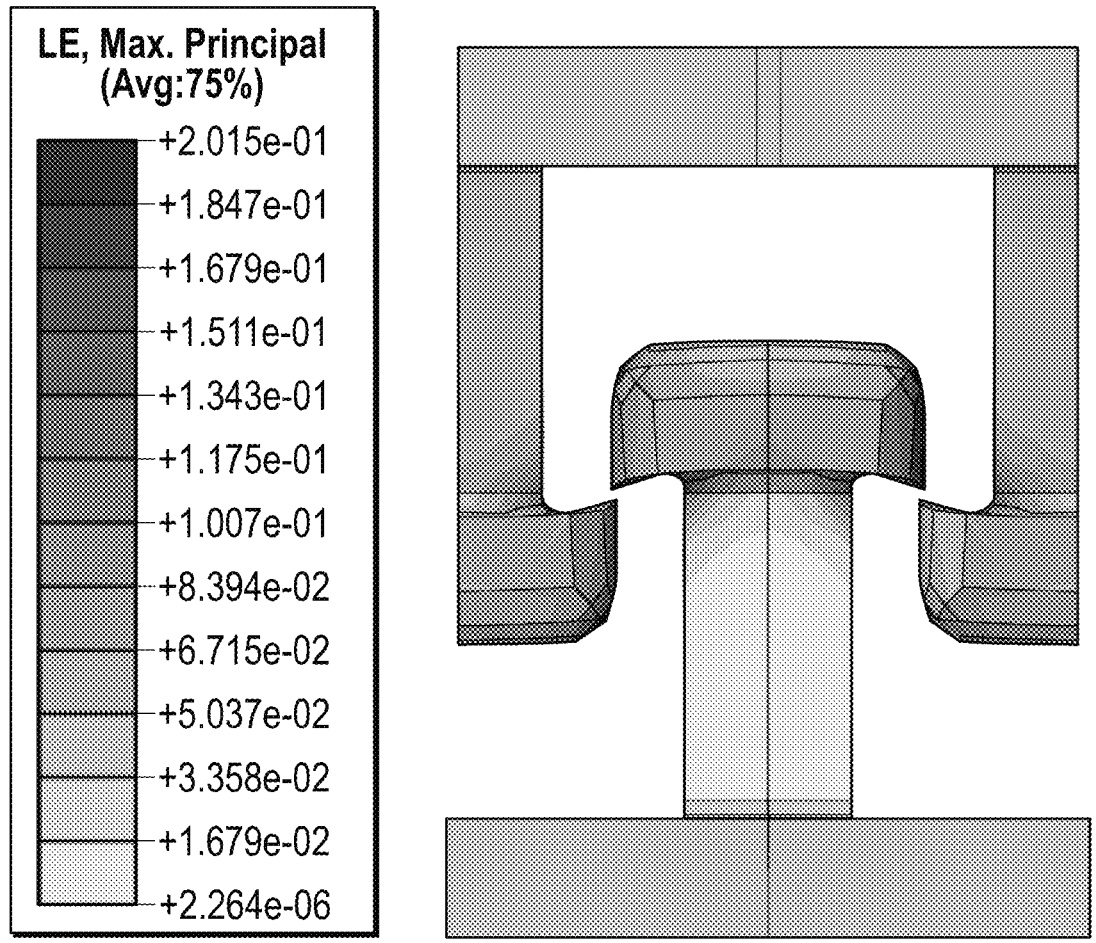
FIG. 4 is a schematic side view of a fastener not according to the present disclosure, with permanent plastic deformation after fastening calculated by Finite Element Modeling depicted by shading.

In some embodiments, the fastening system of the present disclosure is releasably fastenable. As used herein, the term "releasably fastenable" means that the fastener members can alternate between the fastened and unfastened configurations one or more times without destroying the functionality of the fastener. Typically and advantageously, the unique structure of the fastener of the present disclosure can allow for multiple cycles of fastening and unfastening without excessive plastic (i.e., irreversible) deformation of the engaging rail segments. For example, a comparative fastener that includes rail segments, but no posts can undergo fastening when the rail segments are pushed against and past one another for interlocking. The cap portions of the rail segments of comparative fastener exhibit a relative high degree of plastic (i.e., irreversible) deformation after such engagement as shown in FIG. 4. The plastic deformation can limit the ability of the comparative fastener to be unfastened and refastened since the shape of the fastener is altered by the first and successive engagements. In contrast, in the fastening system of the present disclosure when the first and second fastener members undergo fastening, the posts undergo elastic deformation while the cap portions of the rail segments of the first and second fastener members pass by each other as shown in FIG. 3A. The cap portions of the rail segments of the fastener of the present disclosure exhibit a relative low degree of plastic (i.e., irreversible) deformation after engagement as shown in FIG. 3B.

Since fastener 1 illustrated in FIGS. 1A to C and 2A to C is useful, for example, as a self-mating fastener, a shortest distance X8 between one of the posts 6 and one of the base portions 10 of the rail segments 4 in adjacent rows 14, 16 is wide enough to allow the insertion of the cap portion 8 of the rail segments 4. Distance X8 may be substantially the same as X4, as described above in any of the embodiment for X4. In some embodiments, distance X8 is within about 20, 15, or 10 percent of the cap width X4. In some embodiments, a ratio of the distance X8 to the width X1 of the base portion 10 is in a range from 2:1 to 5:1 or from 2:1 to 4:1, or the ratio may be about 3:1. Distances X3 and X5 between one of the post 6 and one of the cap portions 8 of the rail segments 4 in adjacent rows 14, 16 is generally smaller than distance X8 since the cap width X4 is wider than the width of the base portion X1. Some useful distances X3 and X5 are in a range from 0.08 mm to 0.8 mm, 0.1 mm to 0.5 mm, 0.2 mm to 0.4 mm, or 0.2 mm to 0.35 mm. Distances X3 and X5 between a post 6 and two adjacent rows of the cap portions 8 of rail segments 4 need not be equal.

In some embodiments, when the first and second fastener members are fastened, they can slide relative to each other in a direction parallel to the length of the backing. This may be advantageous, for example, if the positioning of the first and second fastener members relative to each is not desirable when the first and second fastener members are initially fastened. To achieve a desirable positioning the first and second fastener members can be slid into place.

The first and second fastener members of a fastening system according to some embodiments of the present disclosure may or may not be connected together. In some embodiments, the first and second fastener members may be connected to two discrete substrates. In some embodiments, the first and second fastener members may be part of the same strip of material in which the first self-mating fastener is folded over to contact the second self-mating fastener.

In the fastener according to the present disclosure, the rail segments, posts, and at least a portion of the backing are integral (that is, generally formed at the same time as a unit, unitary). Fastening elements such as rail segments and upstanding posts on a backing can be made, for example, by feeding a thermoplastic material onto a continuously moving mold surface with cavities having the inverse shape of the fastening elements. The thermoplastic material can be passed between a nip formed by two rolls or a nip between a die face and roll surface, with at least one of the rolls having the cavities. Pressure provided by the nip forces the resin into the cavities. In some embodiments, a vacuum can be used to evacuate the cavities for easier filling of the cavities. The nip has a large enough gap such that a coherent backing is formed over the cavities. The backing may be formed with no holes therethrough. The mold surface and cavities can optionally be air or water cooled before stripping the integrally formed backing and fastening elements from the mold surface such as by a stripper roll.

Suitable mold surfaces for forming fastening elements on a backing include tool rolls such as those formed from a series of plates defining a plurality of cavities about its periphery including those described, for example, in U.S. Pat. No. 4,775,310 (Fischer). Cavities may be formed in the plates by drilling or photoresist technology, for example. Other suitable tool rolls may include wire-wrapped rolls, which are disclosed along with their method of manufacturing, for example, in U.S. Pat. No. 6,190,594 (Gorman et al.). Another example of a method for forming a backing with upstanding fastening elements includes using a flexible mold belt defining an array of fastening element-shaped cavities as described in U.S. Pat. No. 7,214,334 (Jens et al.). Yet other useful methods for forming a backing with upstanding fastening elements can be found in U.S. Pat. No. 6,287,665 (Hammer), U.S. Pat. No. 7,198,743 (Tuma), and U.S. Pat. No. 6,627,133 (Tuma).

If rail segments formed upon exiting the cavities do not have caps, first and second fastener members will not have any closure affinity for each other. Caps can be subsequently formed on the rail segments by a capping method as described in U.S. Pat. No. 5,077,870 (Melbye et al.). Typically, the capping method includes deforming the tip portions of the rail segments using heat and/or pressure. The heat and pressure, if both are used, could be applied sequentially or simultaneously. The formation of rail segments can also include a step in which the shape of the cap is changed, for example, as described in U.S. Pat. No. 6,132,660 (Kampfer) and/or U.S. Pat. No. 6,592,800 (Levitt). For example, one or more of these processes can be useful for changing the shape of the cap portion 8 shown in FIG. 1A to the shape shown in FIG. 2A. The formation of rail segments can also include a step in which the cap is embossed, for example, as described in U.S. Pat. No. 6,000,106 (Kampfer). After one or more of these capping processes, first and second fastener members in a fastening system of the present disclosure can be closed together. The amount of force necessary to close and to peel open the first and second fastener members can be adjusted as desired by tailoring the capping process.

Another useful method for fastening elements on a backing is profile extrusion described, for example, in U.S. Pat. No. 4,894,060 (Nestegard). Typically, in this method a thermoplastic flow stream is passed through a patterned die lip (e.g., cut by electron discharge machining) to form a web having downweb ridges, slicing the ridges, and stretching the web to form separated fastening elements. The ridges may be considered precursors to the fastening elements and exhibit the cross-sectional shape of the rail segments and posts to be formed. The ridges are transversely sliced at spaced locations along the extension of the ridges to form discrete portions of the ridges having lengths in the direction of the ridges essentially corresponding to the length of the fastening elements to be formed. Stretching the backing so that it plastically deforms results in the separation of the fastening elements. In at least one embodiment, slicing the ridges or stretching the web can be optional and result in continuous rail elements and posts.

The fastener of the present disclosure may be made from a variety of suitable materials, including thermoplastics. Examples of thermoplastic materials suitable for making the fastener using the methods described above include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate, and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. In some embodiments, the thermoplastic useful for making the fastener comprises at least one of a polyolefin, a polyamide, or a polyester. In some embodiments, the thermoplastic useful for making the fastener is a polyolefin (e.g., polyethylene, polypropylene, polybutylene, ethylene copolymers, propylene copolymers, butylene copolymers, and copolymers and blends of these materials). In some embodiments, the fastener of the present disclosure is made from a blend of any of these thermoplastic materials and an elastomer. Examples of elastomers useful in such tie layers include elastomers such as ABA block copolymers (e.g., in which the A blocks are polystyrenic and formed predominantly of substituted (e.g., alkylated) or unsubstituted moieties and the B blocks are formed predominately from conjugated dienes (e.g., isoprene and 1,3-butadiene), which may be hydrogenated), polyurethane elastomers, polyolefin elastomers (e.g., metallocene polyolefin elastomers), olefin block copolymers, polyamide elastomers, ethylene vinyl acetate elastomers, and polyester elastomers. Examples of useful polyolefin elastomers include an ethylene propylene elastomer, an ethylene octene elastomer, an ethylene propylene diene elastomer, an ethylene propylene octene elastomer, polybutadiene, a butadiene copolymer, polybutene, or a combination thereof. Elastomers are available from a variety of commercial sources as described below. Any of these elastomers may be present in a blend with any of the thermoplastics in an amount of up to 20, 15, or 10 percent by weight.

The backing of the fastener of the present disclosure may have a variety of thicknesses. In some embodiments, including the embodiments illustrated in FIGS. 1A to 1C and FIGS. 2A to 2C, the thickness (Z4-Z5) of the backing 2 integral with the rail segments 4 and posts 6 may be up to about 300 micrometers (μm), 250 micrometers, or 200 micrometers and at least about 50 micrometers or 75 micrometers. This thickness does not include the heights of the rail segments and posts protruding from the first major surface of the backing. In some embodiments, the thickness of the thermoplastic backing is in a range from 50 to about 300 micrometers, from about 50 to about 200 micrometers, or from about 50 to about 150 micrometers.

In some embodiments, including the embodiments illustrated in FIGS. 1A to 1C and FIGS. 2A to 2C, the rows of rail segments 14 and rows of posts 16 are each independently formed on fillets 12. Referring to FIG. 1B, the fillet thickness Z6 above the backing 2 may be up to about 100 micrometers (μm), 75 micrometers, or 50 micrometers and at least about 10 micrometers or 15 micrometers. This thickness does not include the heights of the rail segments and posts protruding from the first major surface of the backing. In some embodiments, the fillet thickness Z6 is in a range from 10 to about 100 micrometers, from about 15 to about 75 micrometers, or from about 20 to about 50 micrometers. In some embodiments, the backing, excluding the rail segments, posts, and fillets, is substantially uniform in thickness. For a thermoplastic that is substantially uniform in thickness, a difference in thickness between any two points in the backing may be up 5, 2.5, or 1 percent.

In at least one embodiment, rail segments on the first surface of the backing may have a density of at least 10 per square centimeter ($cm^2$) (63 per square inch $in^2$). For example, the density of the rail segments may be at least $100/cm^2$ ($635/in^2$), $248/cm^2$ ($1600/in^2$), $394/cm^2$ ($2500/in^2$), or $550/cm^2$ ($3500/in^2$). In some embodiments, the density of the rail segments may be up to $1575/cm^2$ ($10000/in^2$), up to about $1182/cm^2$ ($7500/in^2$), or up to about $787/cm^2$ ($5000/in^2$). Densities in a range from $10/cm^2$ ($63/in^2$) to $1575/cm^2$ ($10000/in^2$) or $100/cm^2$ ($635/in^2$) to $1182/cm^2$ ($7500/in^2$) may be useful, for example. The density of the rail segments is related to the distance between rail segments X7, measured as the center-to-center distance of the rail segments in adjacent rows as shown in FIG. 1B. A variety of distances X7 between rows of rail segments can be useful. In some embodiments, the distance X7 between rows of rail segments is 0.25 mm to 2.5 mm, 0.5 mm to 1.5 mm, or 0.6 mm to 1.2 mm. The spacing of the rows of rail segments and the posts need not be uniform.

In some embodiments, the backing can be monoaxially or biaxially stretched. Stretching in the machine direction can be carried out on a continuous web of the backing, for example, by directing the web over rolls of increasing speed. Stretching in a cross-machine direction can be carried out on a continuous web using, for example, diverging rails or diverging disks. A versatile stretching method that allows for monoaxial and sequential biaxial stretching of the thermoplastic layer employs a flat film tenter apparatus. Such an apparatus grasps the thermoplastic layer using a plurality of clips, grippers, or other film edge-grasping means along opposing edges of the thermoplastic web in such a way that monoaxial and biaxial stretching in the desired direction is obtained by propelling the grasping means at varying speeds along divergent rails. Increasing clip speed in the machine direction generally results in machine-direction stretching. Stretching at angles to the machine direction and cross-direction are also possible with a flat film tenter apparatus. Monoaxial and biaxial stretching can also be accomplished, for example, by the methods and apparatus disclosed in U.S. Pat. No. 7,897,078 (Petersen et al.) and the references cited therein. Flat film tenter stretching apparatuses are commercially available, for example, from Bruckner Maschinenbau GmbH, Siegsdorf, Germany.

In some embodiments, after stretching, the backing has an average thickness of up to 150 μm, 125 μm, 100 μm, 80 μm, or 75 μm. In some embodiments, the average thickness of the backing after stretching is in a range from 30 μm to 150 μm, 50 μm to 150 μm, or 50 μm to 125 μm. In general, the backing has no through-holes before or after stretching. However, in various embodiments, a pocket in the film with the tooling elements can utilize a flame opening operation where an open flame is applied to the closed end causing the pocket to open, resulting in through-holes.

In some embodiments, the density of the rail segments and/or posts after stretching may be up to about $1182/cm^2$ ($7500/in^2$) or up to about $787/cm^2$ ($5000/in^2$). Densities after stretching in a range from $2/cm^2$ ($13/in^2$) to $1182/cm^2$ ($7500/in^2$), $124/cm^2$ ($800/in^2$) to $787/cm^2$ ($5000/in^2$), $248/cm^2$ ($1600/in^2$) to $550/cm^2$ ($3500/in^2$), or $248/cm^2$ ($1600/in^2$) to $394/cm^2$ ($2500/in^2$) may be useful, for example. Again, the spacing of the spacing of the rows of rail segments and the posts need not be uniform.

In some embodiments, the backing includes a multi-layer construction. The multi-layer construction can include from 2 to 10, 2 to 5, or 2 to 3 layers. The multiple layers can include films, adhesives, and tie layers. The multiple layers can be joined together using a variety of methods including coating, adhesive bonding, and extrusion lamination. In some embodiments, the backing having the protruding rail segments and posts can be made (e.g., using any of the methods described above) from a multilayer melt stream of thermoplastic materials. This can result in the protruding rail segments and posts formed at least partially from a different thermoplastic material than the one predominately forming the backing. Various configurations of upstanding posts made from a multilayer melt stream are shown in U.S. Pat. No. 6,106,922 (Cejka et al.), for example. In some embodiments, the thickness of the backing (including a multi-layer backing) combined with the height of the rail segments is up to 3300, 2000, 1000, 900, 800, 700, 650, 600, 500, 540, or 400 micrometers. In some embodiments, the thickness of the fastening system according to the present disclosure, in which the first and second fastener members are engaged with each other is up to 3300, 2000, 1000, 900, 800, 750, or 700 micrometers.

The bending stiffness of the fastener (e.g., at an axis parallel to the width of the fastener) is influenced by the modulus of the material or materials making up the backing, the thickness of the layer or layers making up the backing, the distance between the structures (including rail segments and posts) on the backing, and the dimension of the fastener in a parallel to the bending axis. In general, materials, thicknesses of the layer or layers in the fastener, and distances between structures can be selected to provide the fastener with a desirable bending stiffness. Advantageously, in many embodiments of the fastener of the present disclosure, the bending stiffness of the fastener is low enough such that the fastener does not unintentionally open when the fastener is bent. In some of these embodiments, the bending stiffness of the fastener in a closed configuration is in a range from 100 mN/mm to 1500 mN/mm, 200 mN/mm to 1200 mN/mm, or 300 mN/mm to 1000 mN/mm as measured by a Flexural Stiffness Test Method, for example, as described in the Examples, below.

In some embodiments, the fastener of the present disclosure and/or the backing of the fastener includes a tie layer. Tie layers can include elastomeric materials or other materials that have lower melting points than the backing integral with the rail segments and posts. Examples of elastomers useful in such tie layers include elastomers such as ABA block copolymers (e.g., in which the A blocks are polystyrenic and formed predominantly of substituted (e.g., alkylated) or unsubstituted moieties and the B blocks are formed predominately from conjugated dienes (e.g., isoprene and 1,3-butadiene), which may be hydrogenated), polyurethane elastomers, polyolefin elastomers (e.g., metallocene polyolefin elastomers), olefin block copolymers, polyamide elastomers, ethylene vinyl acetate elastomers, and polyester elastomers. Examples of useful polyolefin elastomers include an ethylene propylene elastomer, an ethylene octene elastomer, an ethylene propylene diene elastomer, an ethylene propylene octene elastomer, polybutadiene, a butadiene copolymer, polybutene, or a combination thereof. Various elastomeric polymers and other polymers may be blended to have varying degrees of elastomeric properties. For example, any of these elastomeric materials may be present in a range from 50% by weight to 95% by weight in a blend with any of the thermoplastics described above for forming the backing integral with the rail segments and posts.

Many types of elastomers are commercially available, including those from BASF, Florham Park, N.J., under the trade designation "STYROFLEX", from Kraton Polymers, Houston, Tex., under the trade designation "KRATON", from Dow Chemical, Midland, Mich., under the trade designation "PELLETHANE", "INFUSE", VERSIFY", "NORDEL", and "ENGAGE", from DSM, Heerlen, Netherlands, under the trade designation "ARNITEL", from E. I. duPont de Nemours and Company, Wilmington, Del., under the trade designation "HYTREL", from ExxonMobil, Irving, Tex. under the trade designation "VISTAMAXX", and more.

In some embodiments, the fastener of the present disclosure and/or the backing of the fastener includes a layer of a hot melt adhesive. Hot melt adhesives are typically non-tacky at room temperature and use of hot melts can decrease contamination on equipment during the handling of the film and lamination. Suitable hot melt adhesives include those based on ethylene-vinyl acetate copolymers, ethylene-acrylate copolymers, polyolefins, polyamides, polyesters, polyurethanes, styrene block copolymers, polycaprolactone, and polycarbonates and may include a variety of tackifying resins, plasticizers, pigments, fillers, and stabilizers. Examples of suitable hot melt adhesives include those available from 3M Company, St. Paul, Minn., under the trade designation "3M SCOTCH-WELD" hot melt adhesives (e.g., products 3731 B and 3764 PG). In at least one embodiment, the adhesive can be electrically conductive.

Figure 5:
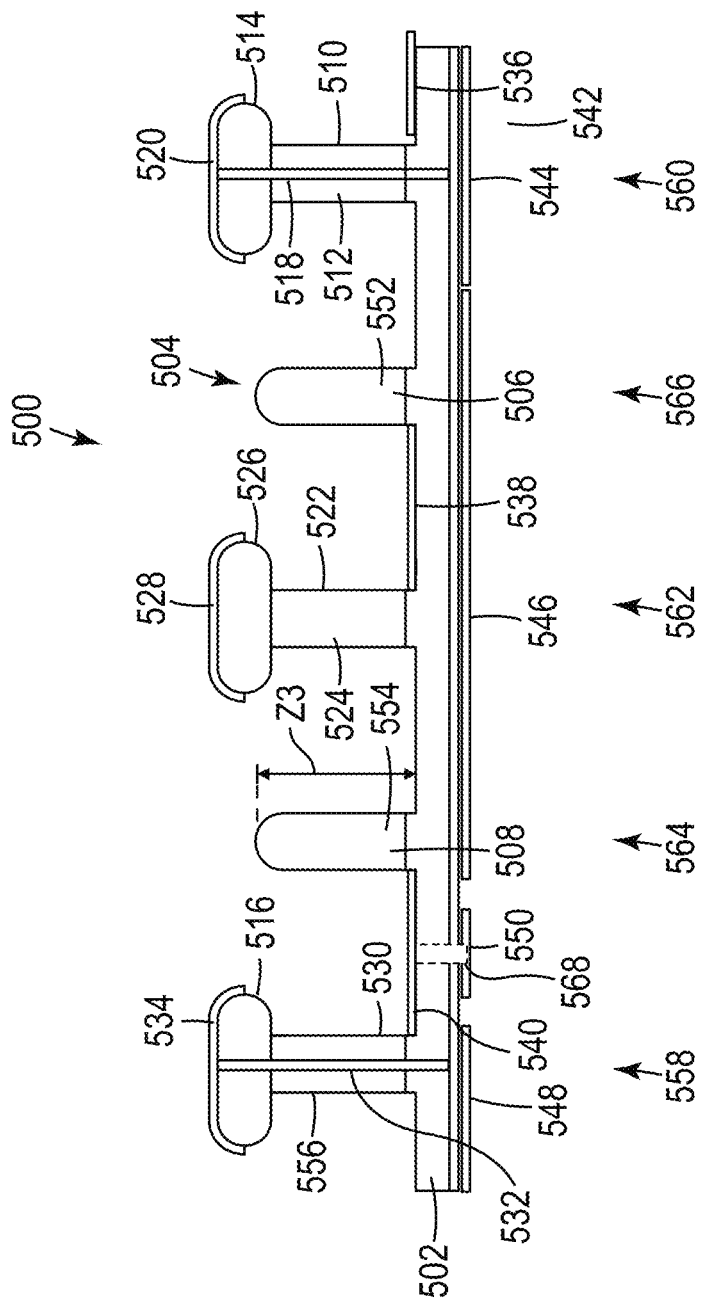
FIG. 5 illustrates a side view of a self-mating fastener in accordance with one embodiment.

FIG. 5 illustrates a self-mating fastener 500 that is similar in structure and configuration to the fastener 1 described herein except self-mating fastener 500 is at least partially electrically conductive and has contact elements disposed on a portion of the self-mating fastener. As shown in self-mating fastener 500, the contact elements include electrically conductive layers disposed on portions of rail elements and backing 502. In at least one embodiment, the contact elements include only electrically conductive layers or conductive stakes on the first side 504. In another embodiment, the contact elements include all electrically conductive layers, and conductive stakes.

The self-mating fastener 500 comprises a first side 504, and a second side 542. In at least one embodiment, the first side 504 has fastener elements protruding distally from a backing 502. The second side 542 can be a side intended to engage with a target surface, such as skin, first electronic device, etc. The second side 542 can also have an optional electrically conductive layer 548 disposed thereon. For example, the electrically conductive layer 548 can be configured to maintain an electrical pathway with the underlying target surface, e.g., a skin surface or electronic device. In at least one embodiment electrically conductive layer 548 is non-continuous. For example, between electrically conductive layer 548 and electrically conductive layer 544 can be electrically insulative layer 546 which can electrically separate the electrically conductive layers.

The first side 504 can include a plurality of post elements (e.g., post element 564, and post element 566). The post elements can be arranged as a row of individual posts. For example, post element 564 can include post 508 and post element 566 can include post 506. The first side 504 can also include a plurality of rail elements (e.g., rail element 558, rail element 562, and rail element 560). Each rail element can include a plurality of rail segments arranged as a row. For example, rail element 558 can include rail segment 530, rail element 562 can include rail segment 522, and rail element 560 can include rail segment 510.

The number of post elements or rail elements is variable, with a different possible configuration options and is shown only as an illustrative example. The post elements are shown in an alternating configuration with the rail elements. For example, post 506 is shown between rail segment 510 and rail segment 522. Post 508 is shown between rail segment 530, and rail segment 522. In at least one embodiment, the post elements can be optional as configurations exist utilizing only a plurality of rail elements.

In at least one embodiment, portions of the plurality of rail elements and/or the plurality of post elements can have at least one electrically conductive layer disposed thereon. For example, the cap portions, and part of the base portion of the rail elements can have the electrically conductive layer disposed thereon, e.g., for the cap portion 514, electrically conductive layer 520; for the cap portion 526, electrically conductive layer 528; and for the cap portion 516, electrically conductive layer 534. In at least one embodiment, the electrically conductive layer can be disposed on a top surface of the cap portion. The electrically conductive layer can cover at least part of the total top surface area or even the entire top surface of the cap portion.

The first side 504 of the backing 502 can have one or more electrically conductive layers disposed between the plurality of rail elements and/or plurality of post elements. For example, electrically conductive layer 536 can be disposed on the backing 502 (first side 504) adjacent to rail element 560 and also be disposed on an adjacent base portion 512 of rail segment 510. In another example, electrically conductive layer 540 can be disposed on the first side 504 between post element 564 and rail element 558. For example, the electrically conductive layer 540 can be disposed on the first side 504 to the right of the rail element 558. The electrically conductive layer can extend continuously in the longitudinal direction in a linear manner and be disjoined with other electrically conductive layers (e.g., electrically conductive layer 538, and electrically conductive layer 540) along the width.

The electrically conductive layer 538 can extend from the base portion 524 to a base portion 552 of the post 506. An electrically conductive layer disposed on the backing 502 can have a non-uniform thickness. Further, the electrically conductive layer between a base portion and the backing 502 can have a corner radius of no greater than 0.25 mm, no greater than 0.1 mm. In at least one embodiment, the electrically conductive layers can be applied via vapor deposition or sputtering.

In at least one embodiment, the base portion of a post or post element can be defined as at least one-quarter of the height Z3 of a post element. For example, the base portion 554 can be at least one-quarter of the height Z3 of post 508. The base portion of a rail element can be defined by a dimension Z2 which is up to a cap portion.

In at least one embodiment, at least one of the rail elements in the self-mating fastener 500 can include a conductive stake therethrough. The conductive stake can penetrate the rail element or rail segment and be approximately centered on the base portion of the rail element. For example, conductive stake 518 can penetrate both the cap portion 514 and the base portion 512 such that the conductive stake 518 forms a conductive path from the electrically conductive layer 520 to the electrically conductive layer 544 of the second side 542.

Likewise, the conductive stake 532 can penetrate the cap portion 516 and the base portion 556 through the electrically conductive layer 548 of the backing 502 to form a conductive path from the electrically conductive layer 534 to the electrically conductive layer 548. In at least one embodiment, the conductive stake can be a rigid element that is electrically conductive. The conductive stake can also be a rail element having a cap portion, and/or a base portion that is electrically conductive. For example, the conductive stake can be a polymer having metalized particles embedded and integrally formed with the rail element such that the cap portion and the second side form an electrical pathway.

In at least one embodiment, electrically conductive layer 534, conductive stake 532, electrically conductive layer 548 form a first electrical pathway. In at least one embodiment, electrically conductive layer 544, conductive stake 518 and electrically conductive layer 520 can form a second electrical pathway. In at least one embodiment, electrically conductive layer 540, electrically conductive layer 550, and conductive stake 568 can form a third electrical pathway. In at least one embodiment, electrically conductive layer 548 can be extended to cover the entire second side 542 of the backing 502, then electrically conductive layer 534, electrically conductive layer 540, and electrically conductive layer 520.

In at least one embodiment, electrically conductive layer 544 and electrically conductive layer 548 are separated by electrically insulative layer 546. Electrically insulative layer 546 can exist as a separate layer or can be integrated with the backing 502 itself, e.g., if the backing 502 can be formed from an electrically insulative material making electrically insulative layer 546 integral with the backing 502. In at least one embodiment, the electrically conductive layer 548 can be electrically distinct from electrically insulative layer 546 and electrically conductive layer 544. For example, electrically conductive layer 544 can be formed from a different material than electrically conductive layer 548 which would give electrically conductive layer 544 different electrical properties suitable for different electrical applications. The electrically insulative layer 546 can be arranged in the longitudinal direction and alternate with the electrically conductive layer 544 and electrically conductive layer 548. In at least one embodiment, electrically conductive layer 548 can be aligned with a rail element 558 (as described in FIG. 6).

In at least one embodiment, the conductive stake is optional. Electrically conductive layer 528 can form a different and separate electrical pathway.

In at least one embodiment, the electrically conductive layer adjacent to a rail segment with a conductive stake, e.g., electrically conductive layer 540, can also be electrically coupled to the top of the cap portion, e.g., electrically conductive layer 534. This can facilitate an electrical connection from the second side 542 of self-mating fastener 500 to a second side of another self-mating fastener. Examples of electrical coupling can include a second conductive stake through the backing 502 or base portion 556 such that the electrically conductive layer 540 forms an electrical pathway to electrically conductive layer 548.

Figure 6:
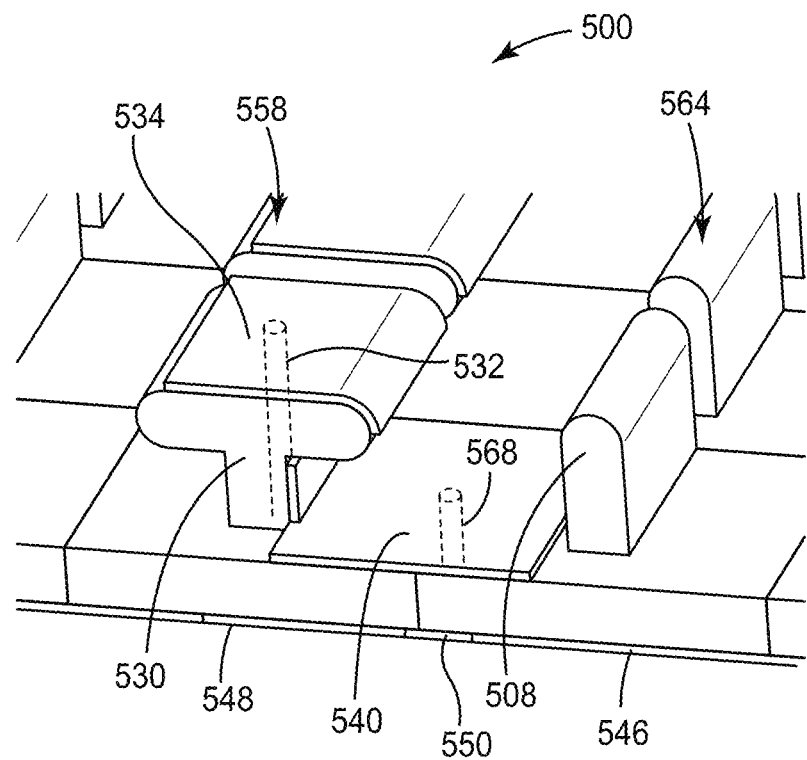
FIG. 6 illustrates a perspective view of the self-mating fastener of FIG. 5 in accordance with one embodiment.

FIG. 6 illustrates a different view of the self-mating fastener 500. The self-mating fastener 500 comprises a post 508, a rail segment 530, an electrically conductive layer 534, an electrically conductive layer 540, an electrically insulative layer 546, and an electrically conductive layer 548. As shown, the electrically conductive layer 540 extends continuously in the longitudinal direction except for the portions of electrically conductive layer 540 that extend onto the base portion of the rail segment 530. In at least one embodiment, each cap portion of a rail segment can have its own electrically conductive layer. For example, electrically conductive layer 534 can be different from an electrically conductive layer for a different rail segment in rail element 558. In at least one embodiment, the electrically conductive layer 540 can be continuous in the longitudinal direction or can also be segmented based on the proximity to the rail segment. As shown herein, the rail element 558 extends in the longitudinal direction and may be alternating with the post element 564 in the width dimension.

Figure 7:
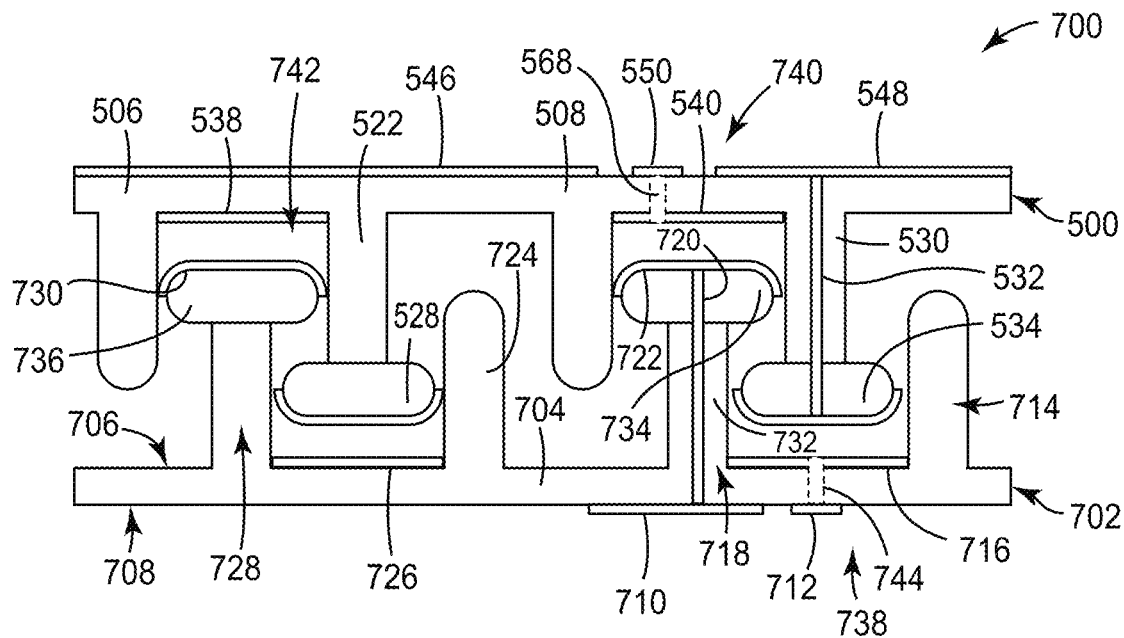
FIG. 7 illustrates a side view of a fastening system in accordance with one embodiment.

FIG. 7 illustrates a fastening system 700 that includes a self-mating fastener 500 as described in FIG. 5 and a second self-mating fastener 702. The second self-mating fastener 702 is configured similarly to self-mating fastener 500.

For example, the second self-mating fastener 702 includes a backing 704. The backing 704 can have a first side 706 and a second side 708. An electrically conductive layer 710 can be disposed on the second side 708. Although not shown, the backing 704 can also have an electrically insulative layer disposed thereon outside the region of the electrically conductive layer 710. The backing 704 can have a plurality of features extending from the first side 706. For example, the backing 704 can have a post element 714, a rail element 718, a post element 724, and a rail element 728 arranged in an alternating fashion. As shown, only some of the rail elements have conductive stakes inserted therethrough. For example, rail element 718 can have a conductive stake 720 inserted and centered through the base portion 732 and the cap portion 734. The conductive stake 720 can contact the electrically conductive layer 722 disposed on a top surface of the cap portion 734. In at least one embodiment, the rail elements and post element can be continuous along the longitudinal direction (unlike the rows of rail segments and posts described in self-mating fastener 500).

In at least one embodiment, electrically conductive layers can be disposed on the first side 706 between the rail element and/or post element. For example, electrically conductive layer 716 can be adjacent to rail element 728 and electrically conductive layer 726 can be adjacent to rail element 718 similar to self-mating fastener 500 in FIG. 5. In at least one embodiment, the electrically conductive layer 730 can be disposed on a top surface of the cap portion 736.

As a system, the self-mating fastener 500 can be slidable (e.g., in the longitudinal direction) with respect to second self-mating fastener 702 while maintaining an electrical connection between, e.g., electrically conductive layer 538 and electrically conductive layer 730; electrically conductive layer 528 and electrically conductive layer 726; electrically conductive layer 722 and electrically conductive layer 540; and electrically conductive layer 534 and electrically conductive layer 716.

The fastening system 700 can have a plurality of electrical pathways. In electrical pathway 738, if the electrically conductive layer 716 is electrically coupled to the conductive stake 720, then electrically conductive layer 548 can be electrically coupled to electrically conductive layer 710 and form a ground electrical connection. Alternatively, in electrical pathway 738, the electrically conductive layer 548, conductive stake 532, electrically conductive layer 534, conductive stake 744, and electrically conductive layer 712 are electrically coupled. In electrical pathway 740, the electrically conductive layer 540 can contact electrically conductive layer 722 to form a longitudinal conductive path from electrically conductive layer 550 to electrically conductive layer 710. In an electrical pathway 742, the electrically conductive layer 538 can contact electrically conductive layer 730 to form a longitudinal conductive path.

In at least one embodiment, the self-mating fasteners of fastening system 700 can be formed from the same methods as described for fastener 1 in FIGS. 1 to 5.

Figure 8:
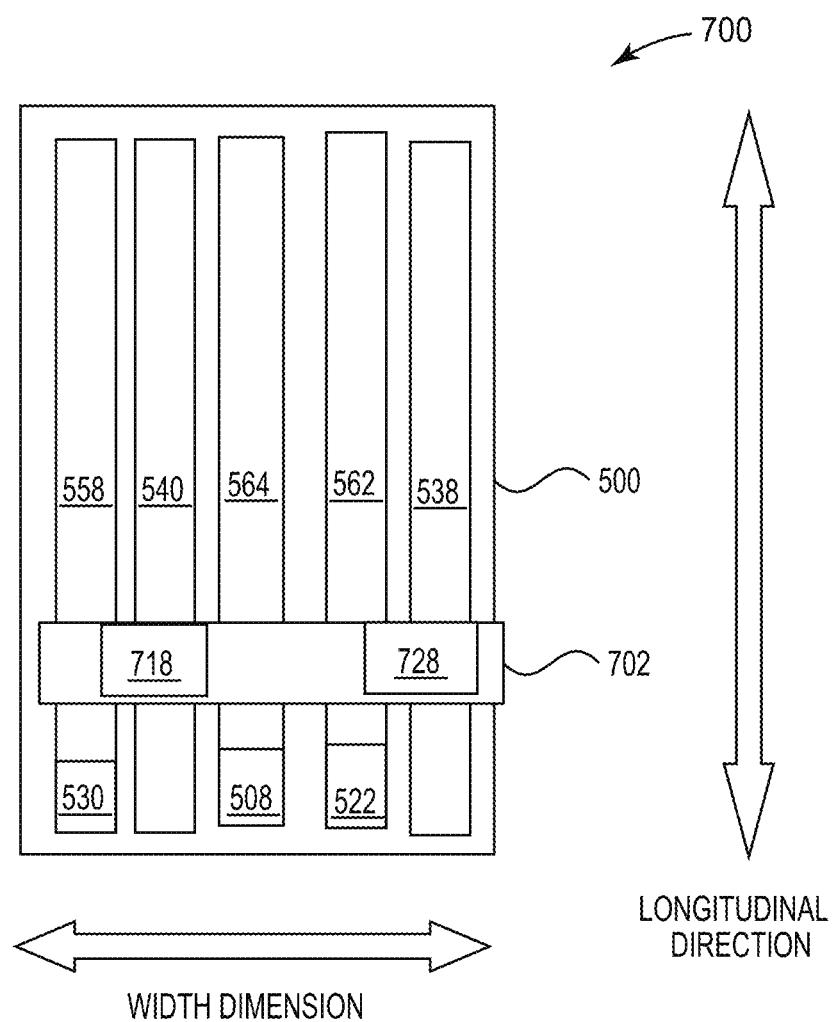
FIG. 8 illustrates a top view of the fastening system of FIG. 7 in accordance with one embodiment.

FIG. 8 illustrates a top view of the fastening system 700 shown with the second self-mating fastener 702 movable about the longitudinal direction but not the width dimension. The rail element 718 is electrically coupled to the electrically conductive layer 540 and mechanically coupled to rail element 558 (including rail segment 530). The rail element 728 is electrically coupled to the electrically conductive layer 538 and mechanically coupled to the rail element 562 (including rail segment 522). The self-mating fastener 500 can have a plurality of rows (shown are three rows including rail element 558, post element 564, and rail element 562 arranged across the width dimension).

In at least one embodiment, an electrically conductive layer can be disposed as a continuous layer (without interruption) along the longitudinal direction. Thus, the self-mating fastener 500 will have rows of longitudinally disposed electrically conductive strips made of the electrically conductive layer. For example, electrically conductive layer 540 can be disposed between rail segment 530 and another rail element in the rail element 558. In at least one embodiment, at least one rail element in the row of rail elements can have a conductive stake such that there is an electrical connection between a device attached to the conductive stake and an electrically conductive layer.

Figure 9A:
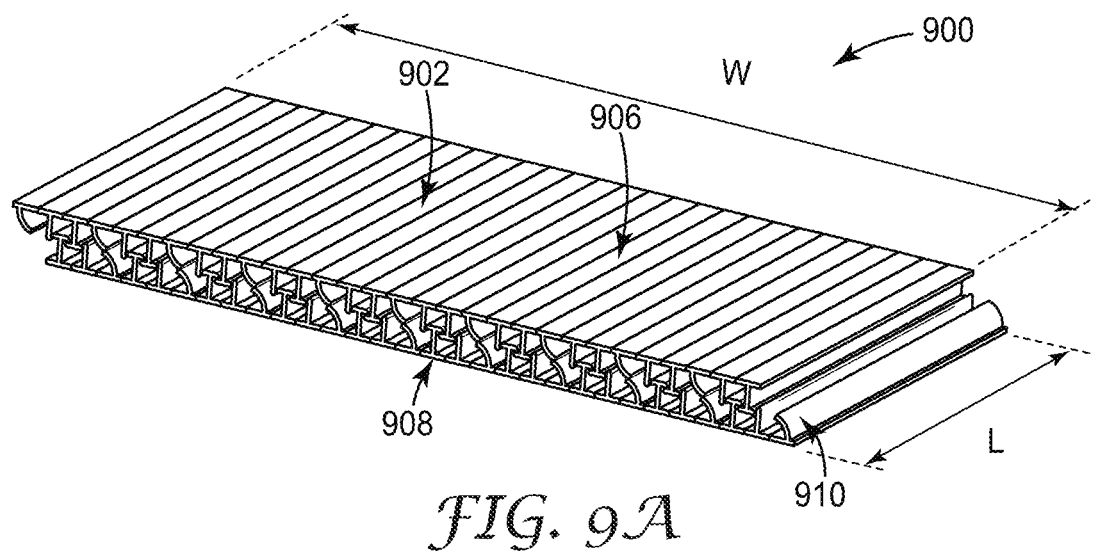
FIG. 9A illustrates a perspective view of a fastening system in accordance with one embodiment.
Figure 9B:
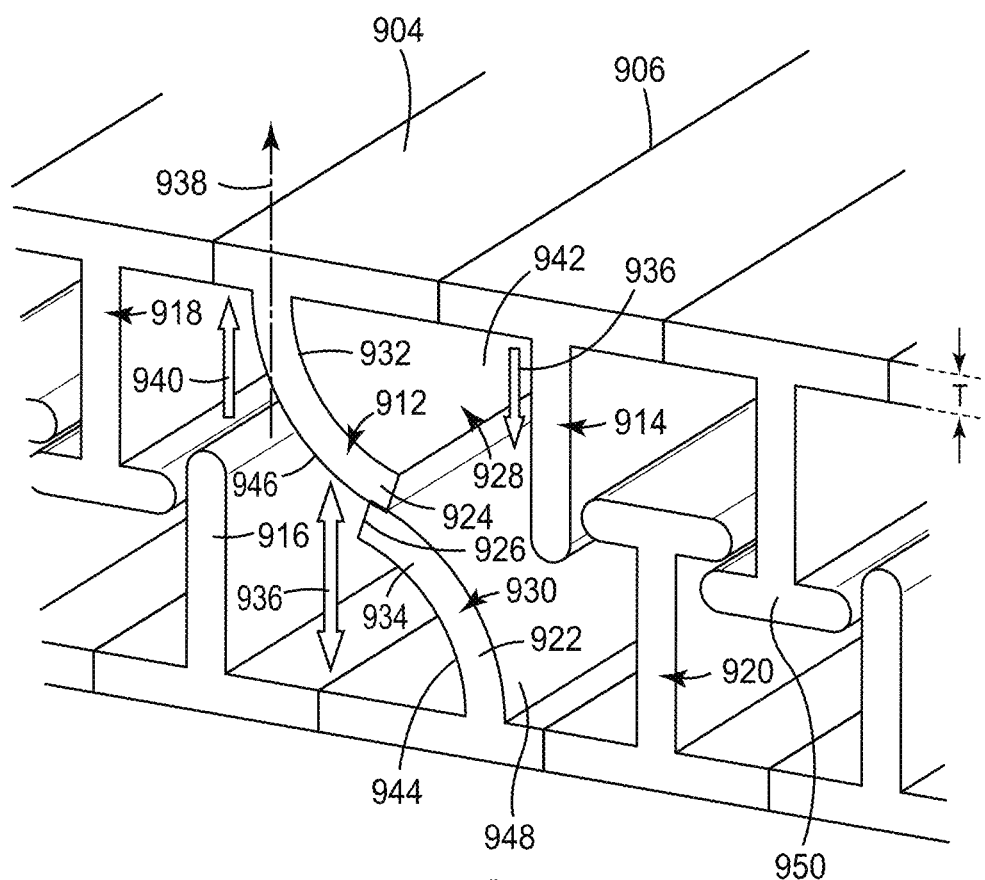
FIG. 9B illustrates a zoomed-in perspective view of the fastening system of FIG. 9A in accordance with one embodiment.

FIG. 9 illustrates an embodiment of a fastening system 900 that includes a self-mating fastener 902, and self-mating fastener 910. In at least one embodiment, the contact element is a separate feature extending from the backing. The self-mating fastener 902 can have rail element 918, contact element 912, and post element 914 extending from backing 906. The self-mating fastener 910 can have a post element 916, contact element 922, and rail element 920 extending from backing 908. In at least one embodiment, both post elements can be I-shaped throughout the length of the post element and both rail elements can be T-shaped throughout the length of the rail element.

One difference between self-mating fastener 902 and the self-mating fastener 500 described herein is that the rail elements and post elements are continuous in the longitudinal direction with no breaks in the width dimension. In at least one embodiment, the backing 906 can be non-uniform and have multiple segments that extend continuously in longitudinal direction and differ in the width dimension. For example, a plurality of backing segments including backing segment 904 can form the backing 906. The backing segment 904 can be different from backing 906 with different electrical properties. In at least one embodiment, the contact element 912 can be disposed on a backing segment 904. In another example, the post element 914, the contact element 912, and the rail element 918 can each extend from a separate backing segment and may be joined together to form the backing 906.

In at least one example, contact element 912 can be formed from an electrically conductive material and have an electrically conductive material as the backing segment 904 while backing 906 is formed from an electrically insulative material. Thus, the backing 906 can have an electrically conductive material adjacent to non-electrically conductive material. In at least one embodiment, each backing can be formed using (profile) extrusion and joined together using bonding techniques as described in U.S. Pat. No. 6,592,800.

In at least one embodiment, the electrically conductive material is extrudable or able to be deposited on a polymeric substance. Examples can include metals, metal polymer compositions, carbon black polymer compositions, conductive polymers such as polyaniline-ES, polyaniline-EB, polyaniline-LS, trans-polyacetylene, poly (p-phenylene), poly(3-vinylperlene), polypyrrole, poly(2,5-bis(3-tetradecylthiophene-2-yl)thieno[3,2-b]thiophene), poly(2-(3-thienyyloxy)ethanesulfonate), polythiophene, or combinations thereof using various dopants and acid combinations.

In at least one embodiment, rail element 920 can engage with another rail element 950 at the bottom of the T-shape on one side and, with the post element 914 on the side of the T-shape. This can allow the self-mating fastener 902 to be slidable along the longitudinal direction with respect to self-mating fastener 910.

For self-mating fastener 902, the contact element 912 is shown having an arc-shape 928. Arc-shapes as referred to herein can refer to a partial arc-shape (as shown in arc-shape 928 or arc-shape 930) or an arch (as described in FIG. 10). The contact element 912 can have a first base portion 932 attached to backing segment 904. Extending distally from the backing segment 904 is distal end 924. The distal end 924 can be offset from the first base portion 932. For example, the distal end 924 can be unaligned with the first base portion 932 along an axis parallel to first axis 938. The first axis 938 can extend perpendicularly from the plane of the backing 906.

The arc-shape 928 can include an inner surface 942 and an outer surface 946. The arcuate dimension of the section the inner surface 942 is less than the arcuate dimension of a section of the outer surface 946. For example, the surface area of the inner surface 942 is less than the surface area of the outer surface 946 for the same length of contact element 912. A resistive force 940, when applied to the contact element 912 toward the backing segment 904 and along first axis 938 can cause the contact element 912 to spring back.

For self-mating fastener 910, the contact element 922 is shown having an arc-shape 930 similar to contact element 912. The contact element 922 can have a first base portion 934 attached to backing 908. Extending distally from the backing 908 is distal end 926. The distal end 926 can be offset from the first base portion 934.

The arc-shape 930 can include an inner surface 944 and an outer surface 948. The dimension of the section the inner surface 944 is less than the dimension of a section of the outer surface 948. For example, the surface area of the inner surface 944 is less than the surface area of the outer surface 948 for the same length of contact element 922. A resistive force 936, when applied to contact element 922 toward the backing 908 along first axis 938 can cause the contact element 922 to spring back.

The contact element 912 can be configured to contact the contact element 922. Both contact elements can have a shape that allows a resistive force in the thickness dimension such that a contact element springs back when downward pressure is applied. The contact elements can be facing the same direction or the opposite direction. For example, contact element 912 is shown with the distal end 924 oriented toward the left (vs the first base portion 932 and relative to rail element 918 when features are pointed upwards) and contact element 922 is shown with the distal end 926 oriented toward the left (vs. First base portion 934 and relative to rail element 920). In at least one embodiment, the distal end 924 can be oriented in the same direction as distal end 926 when the two self-mating fasteners are mated forming a side A-shape.

In at least one embodiment, the outer surface 946 of the distal end 924 can contact the outer surface 948 of distal end 926 such that the resistive force of either contact element 912 or contact element 922 causes each contact element to maintain contact when rail element 950 mates with rail element 918. In at least one embodiment, the inner surface 944 can contact the inner surface 942 when rail element 950 is mated with rail element 918. The contact elements can be slidable in the longitudinal direction with respect to each other.

Although shown as continuous rails in the longitudinal direction, the rail elements and post elements can be segmented as shown in FIG. 1 and FIG. 2. The contact elements can be configured to be continuous such that the conductive path is formed from one end to another end longitudinally in the longitudinal direction.

Figure 10A:
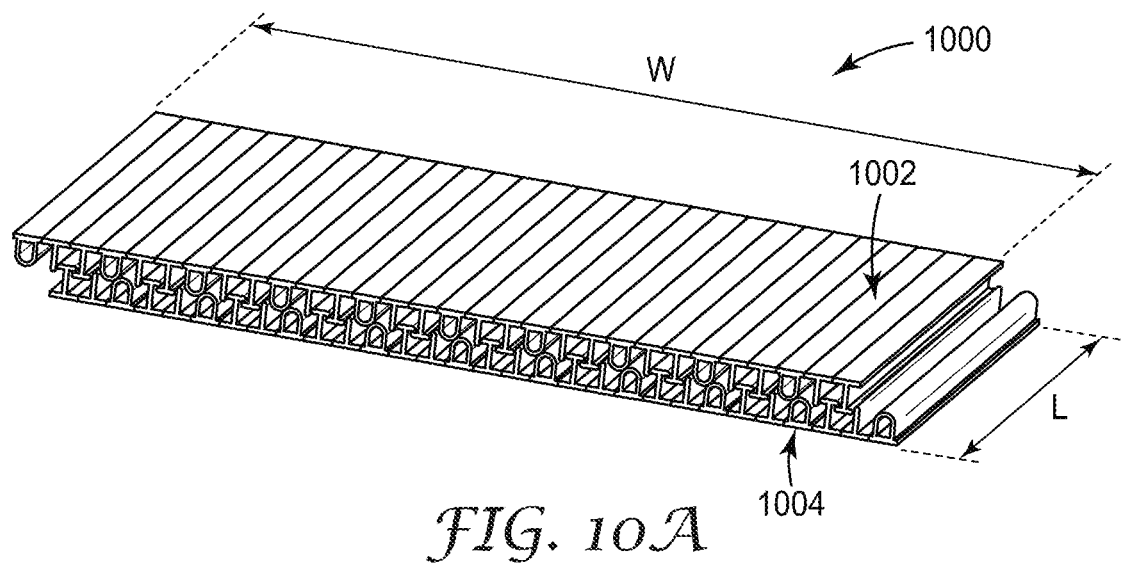
FIG. 10A illustrates a perspective view of a fastening system in accordance with one embodiment.
Figure 10B:
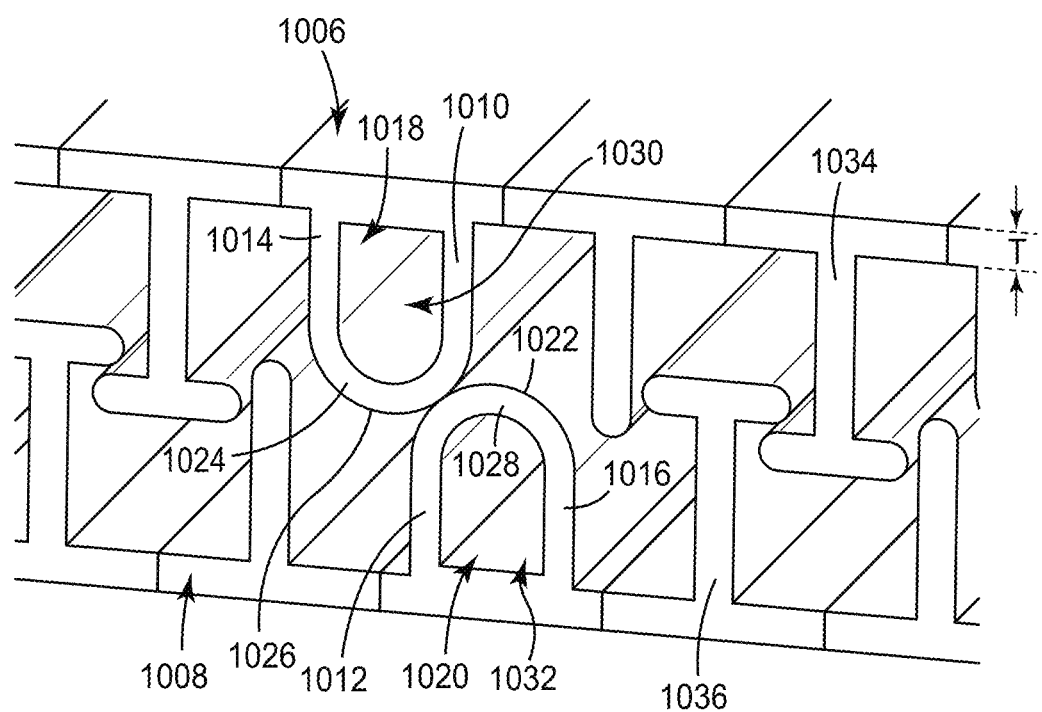
FIG. 10B illustrates a zoomed-in perspective view of the fastening system of FIG. 10A in accordance with one embodiment.

FIG. 10 illustrates another embodiment of a fastening system having different self-mating fasteners. The fastening system 1000 can be configured like the fastening system 900 except having different contact elements. For example, the fastening system 1000 can include a self-mating fastener 1002, and a self-mating fastener 1004. The self-mating fastener 1002 can include a backing 1006 and the self-mating fastener 1004 can include backing 1008. A contact element 1018 can extend from the backing 1006 and contact element 1020 can extend from the backing 1008.

The contact element 1018 and contact element 1020 can be shaped like an (complete) arch extending from the backing 1006 and backing 1008. The contact element 1018 can include first base portion 1010 and second base portion 1014 and the contact element 1020 can include first base portion 1012 and second base portion 1016. The first base portion 1010 is spaced apart from second base portion 1014. The walls of the contact element 1018 can extend distally and converge to a distal end 1024 forming a vertex 1026. Similarly, the walls of the contact element 1020 can extend distally and converge to a distal end 1022 forming vertex 1028. The walls of the contact element 1020 and contact element 1018 can form a tube 1030 and tube 1032. The tube 1030 can fully encapsulate a space. In at least one embodiment, the tube 1030 can be configured to transport or filled with fluids (such as medicament, saline, air, nitrogen, oxygen, water, or biological fluids such as blood or insulin) in the longitudinal direction. Similar to contact element 912, the contact element 1018 and contact element 1020 can provide a spring back force in response to a resistive force from the distal end towards the backing.

When the self-mating fastener 1002 is mated with self-mating fastener 1004, the rail element 1034 from self-mating fastener 1002 can interlock with rail element 1036 on self-mating fastener 1004. The contact element 1018 or contact element 1020 can be of a height that allows contact and a resistive force with respect to contact element 1020 or contact element 1018.

In at least one embodiment, the contact element of fastening system 900 or fastening system 1000 can have a height from the base to the distal end greater than the Z2 dimension described in FIG. 1A. In at least one embodiment, the contact element (either the arc of contact element 912 and contact element 922 from FIG. 9 or the vertex of contact element 1020 and contact element 1018) can have a height from the backing surface to outer surface of the vertex or distal end that is at least 102%, at least 104%, at least 106%, at least 108%, or at least 110% that of the Z2 dimension described in FIG. 1A. The self-mating fastener 1002 can be formed in segments as described in FIG. 9. For example, the self-mating fastener 1002 can have one or more backing segments that are formed using profile extrusion and joined together.

Figure 11:
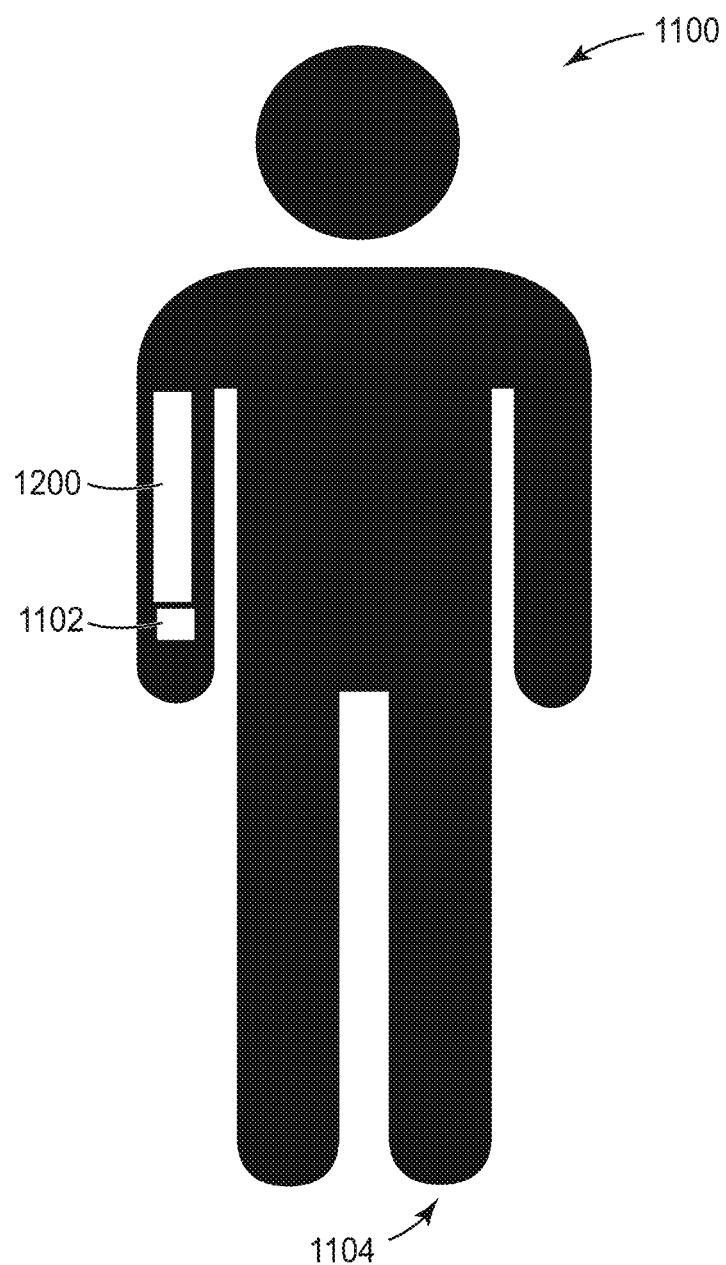
FIG. 11 illustrates an electronic system including a fastening system in accordance with one embodiment.

FIG. 11 illustrates an overview of an electronic system 1100. The electronic system 1100 comprises a mammalian subject 1104, a fastening system 1200, and one or more electronic devices such as first electronic device 1102. The fastening system 1200 can include any combination of the self-mating fasteners described herein. For example, fastening system 1200 can refer to the self-mating fastener 902 paired with the self-mating fastener 1002. The self-mating fastener can include various adhesives or mechanical engagements to releasably attach a backing of the self-mating fastener to the mammalian subject 1104.

In at least one embodiment, the backing can attach to the first electronic device 1102 and the contact elements of a first self-mating fastener can contact the contact elements of a second self-mating fastener. The backing of the second self-mating fastener can be attached to the skin of the mammalian subject 1104. Thus, a conductive path can be formed from the electronic device to the skin via the contact elements or from a first electronic device to a second electronic device via the contact elements.

Figure 12A:
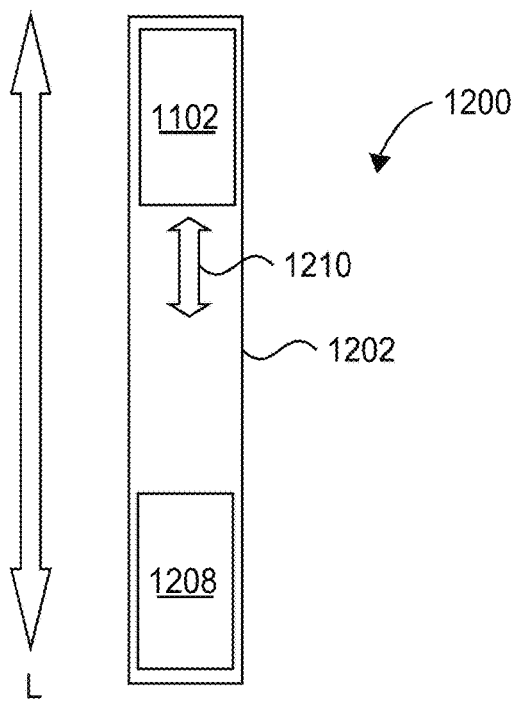
FIG. 12A illustrates an elevational view of a fastening system in accordance with one embodiment.

FIG. 12A illustrates a more detailed view of the fastening system 1200 described herein. The fastening system 1200 can include a self-mating fastener 1202, a first electronic device 1102, and a second electronic device 1208. The self-mating fastener 1202 can form a track such that first electronic device 1102, second electronic device 1208, or both are slidable 1210 in the longitudinal direction when a self-mating fastener 1214 is attached to the electronic device and the first electronic device 1102 is electrically coupled to a portion of the self-mating fastener 1202.

Figure 12B:
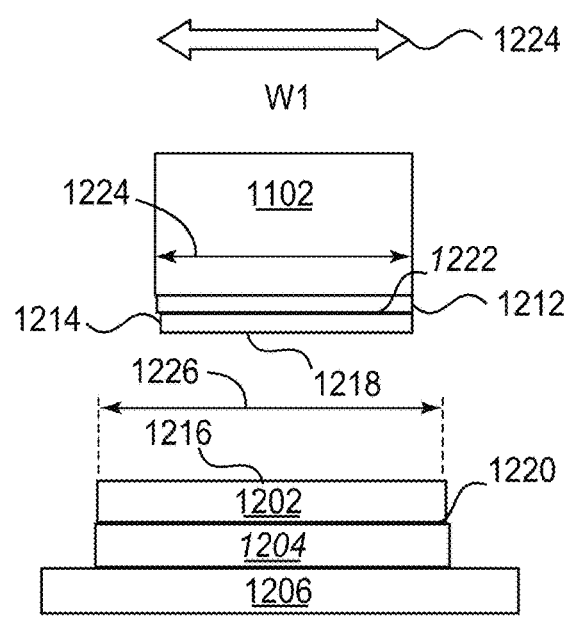
FIG. 12B illustrates a side view of the fastening system of FIG. 12A in accordance with one embodiment.

As shown on FIG. 12B, the self-mating fastener 1202 can have two sides, a first side 1216 and a second side 1220. The first side 1216 (having the rail element and the contact element) can face toward another self-mating fastener (e.g., self-mating fastener 1214). The second side 1220 can be an unfeatured surface that has an adhesive 1204 disposed thereon. In at least one embodiment, the adhesive 1204 can be a skin compatible (pressure sensitive) adhesive that causes minimal irritation to the skin 1206 such as silicone adhesives sold by 3M (Saint Paul, MN). The adhesive 1204 can be optionally covered with a release liner until the self-mating fastener 1202 is ready to be attached to the skin 1206. In at least one embodiment, the width 1226 of the self-mating fastener 1202 is at least that of the adhesive 1204. If grounded, a portion of the featured surface of the self-mating fastener 1202 can be electrically coupled to the skin 1206.

In at least one embodiment, any portion of the backing or backing segment, the rail element, contact element, or post element of any of the fasteners described in this disclosure herein can be transparent or translucent so that the portion is configured to act as a light guide. Examples of construction and materials can be found in U.S. Pat. Nos. 8,758,237; 9,480,760; and 8,877,125, which are incorporated by reference.

Light can be transmitted longitudinally through and along a rail element, contact element, or post element. In another example, the light can be directed toward the skin, i.e., along a perpendicular axis to the skin through the rail element, contact element, post element, and/or backing. In at least one embodiment, the adhesive 1204 to attach the fastener 1202 to the skin 1206 can be optically clear.

The self-mating fastener 1214 can attach to the first electronic device 1102 via an adhesive 1212. In at least one embodiment, one or more features of the self-mating fastener 1214 can electrically couple leads from the first electronic device 1102 through the backing (e.g., via conductive stakes, or leads that penetrate the backing onto the contact element) and onto the featured surface of the self-mating fastener 1214. The self-mating fastener 1214 can have a first side 1218 (having a rail element and other features) and a second side 1222 which is generally unfeatured. The self-mating fastener 1214 can be configured such that the first electronic device 1102 can form an electrical pathway from the first side 1218 to the first electronic device 1102.

The first side 1218 of the self-mating fastener 1214 can face toward the first side 1216 of the self-mating fastener 1202 and mechanically engage with the rail elements and contact elements. Electrical signals can be transmitted from first electronic device 1102 longitudinally through self-mating fastener 1202 to second electronic device 1208 via an electrical pathway. The width 1224 of the first electronic device 1102 can be at least the width of the self-mating fastener 1214. In at least one embodiment, the width 1224 can be no greater than width 1226.

Figure 13:
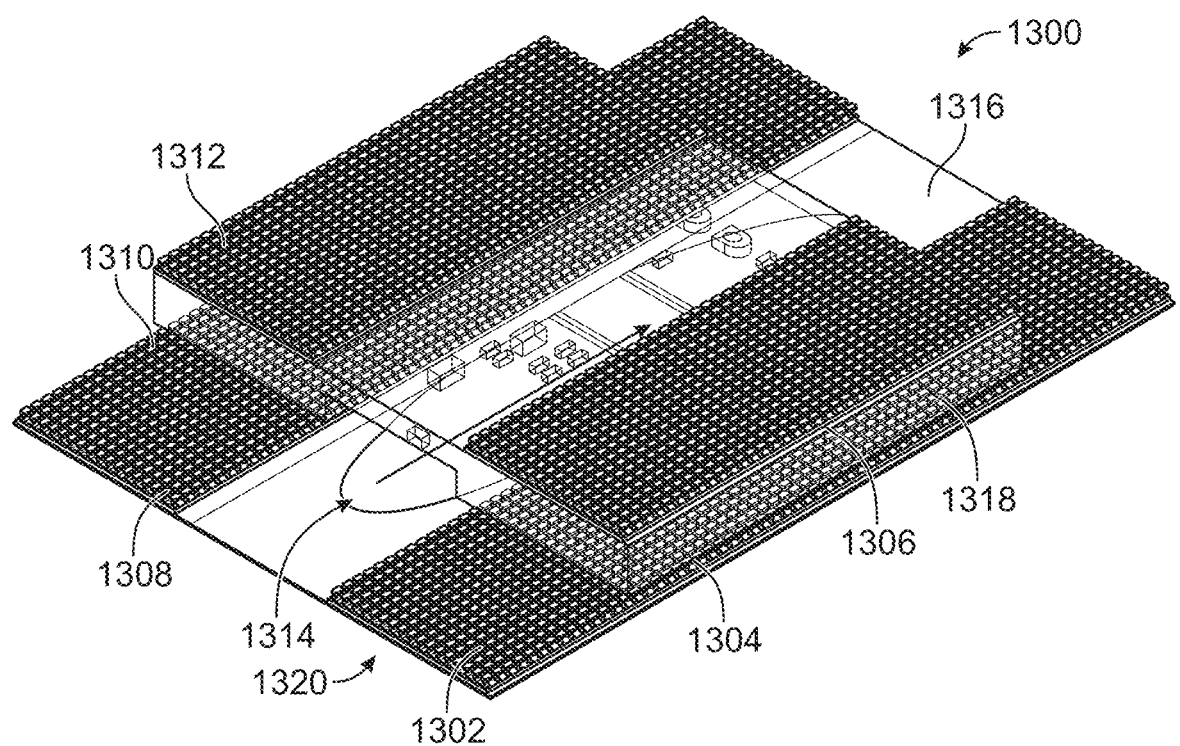
FIG. 13 illustrates an electronic system in accordance with one embodiment.

FIG. 13 illustrates an electronic system 1300 similar to electronic system 1100. The electronic system 1100 includes a plurality of self-mating fasteners disposed on a substrate (e.g., substrate 1316). Each self-mating fastener can have at least one contact element as described herein. The substrate 1316 can be configured to be conformable to skin 1320 and strong enough to support the self-mating fastener 1302 or self-mating fastener 1308 while adhered to the skin 1320.

The electronic system 1300 shows a self-mating fastener 1302 and self-mating fastener 1308 disposed on substrate 1316. The substrate 1316 can be a transparent medical dressing such as a hydrocolloid dressing. An example of the transparent medical dressing is commercially available under the trade designation Tegaderm from 3M (Saint Paul, MN). The self-mating fastener can be secured to the substrate 1316 with an adhesive or can be formed therein.

In at least one embodiment, the substrate 1318 has a first electronic device 1314 secured thereon. In at least one embodiment, the first electronic device 1314 can be secured to the substrate 1318. For example, the substrate 1318 can be a printed circuit board.

The self-mating fastener 1302 can mate with self-mating fastener 1304, and self-mating fastener 1308 can mate with self-mating fastener 1310. Self-mating fastener 1310 and self-mating fastener 1304 can be disposed on substrate 1318 such that substrate 1318 can be slidable along a track formed by self-mating fastener 1302 and self-mating fastener 1308 in the longitudinal direction. The substrate 1318 can be more rigid relative to substrate 1316. Further, electrical signals from the first electronic device 1314 can be transmitted along self-mating fastener 1302 and self-mating fastener 1308 and also self-mating fastener 1312 and self-mating fastener 1306.

In at least one embodiment, the substrate 1318 can support a second electronic device or other substrates. For example, substrate 1318 can have self-mating fastener 1306 and self-mating fastener 1312 disposed thereon. The self-mating fastener 1306 and self-mating fastener 1312 can be configured to mate with other self-mating fasteners on another substrate such that the substrates are stacked and movable relative to each other and form electrical connections sufficient to transmit electrical signals along electrical pathways.

LIST OF ILLUSTRATIVE EMBODIMENTS

1. A self-mating fastener comprising:
a backing having a first side; and
a rail element protruding perpendicularly from the first side of the backing, the rail element extends in a longitudinal direction along the backing;
an electrically conductive contact element proximate to the rail element;
wherein the rail element has a base portion attached to the first side of the backing and a cap portion distal from the backing,
wherein the cap portion has a cap width that is greater than a width of the base portion,
wherein the cap portion overhangs the base portion on opposing sides.

2. The self-mating fastener of embodiment 1, wherein the rail element comprises a plurality of rail segments arranged in a row.

3. The self-mating fastener of any of the preceding embodiments, wherein the backing has a length, a width, and a thickness.

4. The self-mating fastener of any of the preceding embodiments, wherein the thickness of the backing combined with a height of the rail segments is up to 3300 micrometers.

5. The self-mating fastener of any of the preceding embodiments, wherein the thickness of the backing combined with the height of the rail segments is no greater than 1500 micrometers.

6. The self-mating fastener of any of the preceding embodiments, wherein the thickness of the backing combined with the height of the rail segments is no greater than 500 micrometers.

7. The self-mating fastener of any of the preceding embodiments, further comprising a post element extending perpendicularly from the first side of the backing and extending in a longitudinal direction along the backing and adjacent to the rail element.

8. The self-mating fastener of embodiment 7, wherein the post element has a height that is no greater than the height of the rail element.

9. The self-mating fastener of embodiment 7, wherein the post element comprises a plurality of posts that are arranged in a row, a number of posts in one of the rows of posts is more than a number of rail segments in one of the rows of rail segments.

10. The self-mating fastener of embodiment 9, wherein the length of the base portion of the rail segments is greater than a length of the posts.

11. The self-mating fastener of embodiment 10, wherein a length of the base portion of the rail segments in the longitudinal direction is at least two times the length of the posts in the longitudinal direction.

12. The self-mating fastener of embodiment 11, wherein the length of the base portion of the rail segments is at least three times the length of the posts.

13. The self-mating fastener of embodiment 9, wherein a number of posts in one of the rows of posts is at least 1.5 times a number of rail segments in one of the rows of rail segments.

14. The self-mating fastener of embodiment 9, wherein the number of posts in one of the rows of posts is at least twice the number of rail segments in one of the rows of rail segments.

15. The self-mating fastener of embodiment 9, wherein each of the posts has at least one of a height-to-width aspect ratio that is at least 1.5:1 or a height-to-length aspect ratio that is at least 1.5:1.

16. The self-mating fastener of embodiment 9, wherein each of the posts has at least one of a height-to-width aspect ratio that is at least 2:1 or a height-to-length aspect ratio that is at least 2:1.

17. The self-mating fastener of embodiment 9, wherein the row of posts has a lower bending stiffness than the row of rail segments.

18. The self-mating fastener of embodiment 9, wherein the height of the posts is no greater than 95 percent of the height of the rail segments.

19. The self-mating fastener of embodiment 9, wherein the post has a base attached to the backing and a distal end, wherein the distal end has a cross-sectional area that is less than or equal to a cross-sectional area of the base.

20. The self-mating fastener of embodiment 9, wherein a shortest distance in the width dimension between one of the posts and one of the base portions of the rail segments in adjacent rows is no greater than 20 percent of the cap width.

21. The self-mating fastener of embodiment 9, wherein the self-mating fastener has at least three of the rows of rail segments alternating with at least three of the rows of posts.

22. The self-mating fastener of embodiment 21, wherein the self-mating fastener has at least five of the rows of rail segments alternating with at least five of the rows of posts.

23. The self-mating fastener of embodiment 9, further comprising a tie layer on a major surface of the backing opposite the rows of rail segments and rows of posts.

24. The self-mating fastener of embodiment 23, wherein the tie layer comprises a polyolefin elastomer.

25. The self-mating fastener of any of the preceding embodiments, wherein the base portion has a length that is greater than the width of the base portion.

26. The self-mating fastener of embodiment 25, wherein a ratio of the length of the base portion to the width of the base portion is at least 2:1.

27. The self-mating fastener of embodiment 26, wherein a ratio of the length of the base portion to the width of the base portion is at least 5:1.

28. The self-mating fastener of embodiment 27, wherein a ratio of the length of the base portion to the width of the base portion is at least 10:1.

29. The self-mating fastener of any of the preceding embodiments, wherein the base portion is continuous and oriented in a longitudinal direction.

30. The self-mating fastener of any of the preceding embodiments, wherein the cap portion overhangs the base portion on all sides.

31. The self-mating fastener of any of the preceding embodiments, wherein the cap portion overhangs the base portion at amount of at least 25 micrometers on opposing sides.

32. The self-mating fastener of any of the preceding embodiments, wherein the backing is formed without through-holes.

33. The self-mating fastener of any of the preceding embodiments, wherein the contact element extends perpendicularly from the first side of the backing and adjacent to the rail element.

34. The self-mating fastener of embodiment 33, wherein the backing comprises one or more backing segments that are joined together.

35. The self-mating fastener of embodiment 34, wherein the contact element extends perpendicularly from the first side of a first backing segment, and a rail element extends perpendicularly from the first side of a second backing segment.

35a. The self-mating fastener of embodiment 35, wherein the contact element and the first backing segment are integrally formed.

36. The self-mating fastener of any of the preceding embodiments, wherein the contact element is configured to provide resistive force in response to downward pressure from a distal end of the contact element toward the backing.

37. The self-mating fastener of any of the preceding embodiments, wherein the contact element comprises a distal end and a first base portion.

38. The self-mating fastener of any of the preceding embodiments, wherein the distal end is not aligned with a first axis extending perpendicularly from the first base portion.

39. The self-mating fastener of embodiment 38, wherein the contact element forms an arc-shape having an inner surface and an outer surface, the outer surface has a greater area than the inner surface.

40. The self-mating fastener of embodiment 39, wherein a portion of the outer surface comprises an electrically conductive layer.

41. The self-mating fastener of embodiment 39, wherein the arc-shape is a partial arc-shape having a radius of less than 180 degrees.

42. The self-mating fastener of embodiment 37, wherein the contact element comprises the first base portion and a second base portion both extending from the backing and the distal end is a vertex.

43. The self-mating fastener of embodiment 42, wherein the contact element extends in a longitudinal direction along the backing and has a height from the backing to the vertex that is at least the height of the base portion and no greater than two times the base portion.

44. The self-mating fastener of embodiment 42, wherein the first base portion and the second base portion each have an inner surface, the inner surfaces of the first base portion and second base portion, and the vertex forms a tube in the longitudinal direction.

45. The self-mating fastener of embodiment 44, wherein the tube is filled with a medicament or biological fluids.

46. The self-mating fastener of embodiment 33, wherein the contact element is configured to provide spring back force in response to downward force applied from a distal end of the contact element toward the backing.

47. The self-mating fastener of embodiment 46, wherein the contact element has a height from backing to the distal end that is at least a height of a base portion of the rail element.

48. The self-mating fastener of any of the preceding embodiments, wherein the contact element comprises an electrically conductive material, but the rail element does not comprise the electrically conductive material.

49. The self-mating fastener of embodiment 48, wherein the electrically conductive material comprises carbon black, a metal composition, a conductive polymer, or combinations thereof.

50. The self-mating fastener of any of the preceding embodiments, wherein the contact element comprises a first electrically conductive layer disposed on a portion of the cap portion and on the first side of the backing adjacent to a base portion.

50a. The self-mating fastener of any of the preceding embodiments, wherein the first electrically conductive layer is disposed on the entire first side of the backing including the cap portion, the post element, and the areas adjacent to the post element.

51. The self-mating fastener of embodiment 50, wherein the contact element is formed as an electrically conductive layer on a surface of the post element.

52. The self-mating fastener of any of the preceding embodiments, wherein the backing has a second side, the first contact element comprises a second electrically conductive layer disposed on a portion of the second side in the longitudinal direction and aligned with the rail element, further comprising conductive stake electrically coupling the first electrically conductive layer and the second electrically conductive layer.

53. The self-mating fastener of any of the preceding embodiments, wherein the second side is unfeatured.

54. The self-mating fastener of any of the preceding embodiments, further comprising:
a second rail element extending distally from the first side of the backing, the second rail element comprises a cap portion;
a second contact element comprising:
a first electrically conductive layer formed on a portion of the cap portion,
a second electrically conductive layer formed on the second side of the backing, and
a conductive stake formed to electrically couple the first electrically conductive layer and the second electrically conductive layer to form a conductive path.

55. The self-mating fastener of any of the preceding embodiments, further comprising a third contact element comprising:
a first electrically conductive layer disposed on the first side of the backing adjacent the rail element and on a portion of the base portion of the rail element;
a second electrically conductive layer disposed on the second side of the backing and aligned in the width dimension with the first electrically conductive layer;
a conductive stake electrically coupling the first electrically conductive layer with the second electrically conductive layer across the thickness of the backing.

56. The self-mating fastener of any of the preceding embodiments, wherein the first contact element is electrically insulated from the second contact element and the third contact element.

57. The self-mating fastener of any of the preceding embodiments, wherein a post element is disposed between the second rail element and the first rail element along the width dimension.

58. The self-mating fastener of embodiment 57, wherein the cap width is greater than a distance between the post element and the rail element.

58a. The self-mating fastener of any of the preceding embodiments, wherein at least a portion of the backing, the contact element, rail element, or post element can act as a light guide.

58b. The self-mating fastener of embodiment 58a, wherein the backing has an optically clear adhesive disposed on the second side.

58c. The self-mating fastener of embodiment 58b, wherein a portion of the backing is transparent.

59. A fastening system comprising:
a first self-mating fastener, and a second self-mating fastener, both the first self-mating fastener and the second self-mating fastener are configured according to the self-mating fastener of embodiments 1 to 58.

60. The fastening system of embodiment 59, wherein the base portion has a length that is greater than the width of the base portion.

61. The fastening system of embodiment 60, wherein when the first and second fasteners are fastened, they can slide relative to each other in a direction parallel to the length of the backing.

62. The fastening system of embodiment 61, wherein when the first and second fasteners undergo fastening, the posts bend away from the rail segments while the cap portions of the rail segments of the first and second fastening members pass by each other and then return to their original positions after the first and second fasteners are fastened.

63. The fastening system of any of the preceding embodiments, wherein the backing of at least one of the first self-mating fastener or second self-mating fastener is formed without through-holes.

64. The fastening system of any of the preceding embodiments, wherein the contact elements of the first and second fasteners are frictionally resistive toward each other such that force is applied to the contact elements of the first and second self-mating fasteners when sliding relative to each other.

65. The fastening system of any of the preceding embodiments, wherein the rail element of the first fastener is aligned with the rail element of the second fastener such that when fastened, the cap of the first rail element engages the cap of the second rail element.

66. The fastening system of embodiment 65, wherein part of the cap portion proximate an overhang of the cap portion of a rail element of the first fastener contacts the base portion of the rail element of the second fastening member.

67. The fastening system of any of the preceding embodiments, wherein the contact elements of the first and second fasteners contact each other upon fastening of the rail segments and form an electrical connection.

68. The fastening system of embodiment 67, wherein each of the first fastener and the second fastener includes at least two conductive paths that are electrically insulated from each other.

69. The fastening system of embodiment 68, wherein the first fastener comprises a first contact element and a third contact element, the second fastener comprises a second contact element and a fourth contact element, wherein the first contact element and the second contact element are releasably coupled, and the third contact element and the fourth contact element are releasably coupled, the first contact element is electrically insulated from the second contact element.

70. The fastening system of embodiment 67, further comprising a plurality of conductive paths.

71. The fastening system of embodiment 70, wherein at least one of the conductive paths is formed from the second side of the first self-mating fastener to the second side of the second self-mating fastener.

72. The fastening system of embodiment 71, wherein at least one of the conductive paths is formed through a backing segment of the first self-mating fastener.

73. The fastening system of any of the preceding embodiments, further comprising a pressure sensitive adhesive disposed on the second side of the backing of at least one of the first self-mating fastener or the second self-mating fastener.

74. An electronic system, comprising:
the fastening system of any of embodiments 59 to 73, and a first electronic device, wherein the first fastener is disposed on the first electronic device and electrically coupled to the first electronic device.

75. The electronic system of embodiment 74, wherein the first electronic device is configured measure one or more physiological parameter.

76. The electronic system of embodiment 75, wherein the first electronic device is configured to receive electrical power through the first self-mating fastener and the first electronic device is electrically coupled to the second side of the first self-mating fastener.

77. The electronic system of embodiment 76, further comprising a second self-mating fastener electrically coupled to the first electronic device through the first self-mating fastener.

78. The electronic system of embodiment 77, wherein the second self-mating fastener has a greater length than the first self-mating fastener and the first self-mating fastener is slidable along the second self-mating fastener while maintaining an electrical connection between the two fastener members.

79. The electronic system of embodiment 78, further comprising a third fastener member that is electrically coupled to a second electronic device and slidable with respect to the second fastener, the first electronic device is electrically coupled to the second electronic device via the second fastener.

80. The electronic system of embodiment 79, wherein the second electronic device is a battery or a sensor.

81. The electronic system of embodiment 80, wherein the second electronic device provides an electrical signal to the first electronic device via a first electrical pathway defined partly by a first contact element in the second fastener and receives an electrical charge from the first electronic device by a second contact element in the second fastener.

82. The electronic system of embodiment 81, wherein the second fastener is configured to transport fluids from the first electronic device to the second electronic device.

83. The electronic system of embodiment 82, further comprising a mammalian subject, wherein the second electronic device or the second fastener is fluidically coupled to the skin of the mammalian subject sufficient to receive bodily fluids from the mammalian subject.

84. The electronic system of embodiment 83, wherein the second side of the second fastener, when attached to the skin, establishes a ground connection from the skin to the second side of the first self-mating fastener.

85. A method of making the self-mating fastener of any of embodiments 1 to 58, comprising:
   extruding a rail element and first backing segment along a longitudinal direction wherein the rail element has a cap width that is less than the width of the backing segment, the backing segment is formed of an electrically insulated material;
   extruding a contact element and second backing segment along a longitudinal direction, wherein the contact element and second backing segment are formed from an electrically conductive material;
   joining the first backing segment and the second backing segment together.

86. A method of using the fastening system of any of embodiments 59 to 84, comprising:
   adhering a second side of the first self-mating fastener to a first electronic device such that the contact element of the first self-mating fastener is electrically coupled to a portion of the first electronic device; and
   adhering a second side of the second self-mating fastener to the skin of a mammalian subject, wherein the second self-mating fastener has a greater length along the longitudinal direction than the first self-mating fastener;
   connecting the first side of the first self-mating fastener to the first side of the second self-mating fastener by pressing with a downward force on the first electronic device.

87. A method of using the fastening system of embodiment 86, further comprising sliding the first electronic device along the second self-mating fastener.

88. A kit comprising:
a first self-mating fastener of any of embodiments 1 to 59; and a package.

89. The kit of embodiment 88, wherein the first self-mating fastener is continuous and in a rolled configuration sufficient to fit inside of the package.

90. The kit of embodiment 88, further comprising a first electronic device.

91. The kit of embodiment 88, further comprising a second self-mating fastener.

92. The kit of embodiment 88, further comprising an extensible or rigid extension of a self-mating fastener.

The phrase "comprises at least one of" followed by a list refers to comprising any one of the items in the list and any combination of two or more items in the list. The phrase "at least one of" followed by a list refers to any one of the items in the list or any combination of two or more items in the list.

As used herein, the term "or" is generally employed in its usual sense including "and/or" unless the content clearly dictates otherwise.

The term "and/or" means one or all of the listed elements or a combination of any two or more of the listed elements.

The term "machine direction" (MD) as used herein denotes the direction of a running web of material during a manufacturing process. When a strip is cut from a continuous web, the dimension in the machine direction corresponds to the length "L" of the strip. The terms "machine direction" and "longitudinal direction" may be used interchangeably. The term "cross-machine direction" (CD) as used herein denotes the direction which is essentially perpendicular to the machine direction. When a strip is cut from a continuous web, the dimension in the cross-machine direction corresponds to the width "W" of the strip. Accordingly, the term "width" typically refers to the shorter dimension in the plane of the first side of the backing (featured side), which is the surface bearing the rail segments and posts. As used herein the term "thickness" usually refers to the smallest dimension of the fastener, which is the dimension perpendicular to the first side of the backing.

The term "alternating" as used herein refers to one row of rail segments being disposed between any two adjacent rows of posts (i.e., the rows of posts have only one row of rail segments between them) and one row of posts being disposed between any two adjacent rows of rail segments.

The term "perpendicular" as used herein to refer to the relationship between the backing and the rail segments and/or posts includes substantially perpendicular. "Substantially perpendicular" means that the planes defined by the backing and a row of rail segments or posts can deviate from perpendicular by up to 10 (in some embodiments, up to 7.5 or 5) degrees.

The term "physiological parameter" refers to any measurement relating to a bodily function of a mammal. Examples include temperature, heart rate, ECG, blood pressure, blood flow, blood volume, respiration, skin condition, shivering, blood sugar, or combinations thereof.

The term "through-holes" refers to a technique in which protrusions on discrete components are inserted through holes in a substrate.

The term "slidable" refers to an ability to slide relative to another component in the longitudinal direction.

The term "tube" refers to a hollow elongated cylinder-type shape

The term "electrically conductive" refers to an ability to conduct an electric current. Electrically conductive materials have an electrical conductivity of at least 2 Siemens per centimeter.

The term "electrically insulated" or "electrically insulative" refers to how strongly that material opposes the flow of electric current. Electrically insulated means having a surface resistivity of at least $10^{\wedge}13$ Ohm/sq.

The term "electrically conductive layer" refers to a uniform layer of electrically conductive material or an uneven coating of electrically conductive material such that the entire coating is conductive from one end to the other end.

The term "mammalian subject" refers to any animal of the Mammalia, a large class of warm-blooded vertebrates having mammary glands in the female, a thoracic diaphragm, and a four-chambered heart. The class includes the whales, carnivores, rodents, bats, primates, humans, etc.

The term "electronic device" refers to a device depending on the principles of electronics and using the manipulation of electron flow for its operation. Electronic devices may be used in or facilitate monitoring one or more physiological parameters of a mammalian subject. Examples of electronic devices include heart rate monitors, wearable computers, insulin pumps, batteries, sensors, etc.

The term "frictionally resistive" refers to the cap normal force multiplied by the friction coefficient of the base polymers on themselves.

As used herein in connection with a measured quantity, the term "about" refers to that variation in the measured quantity as would be expected by the skilled artisan making the measurement and exercising a level of care commensurate with the objective of the measurement and the precision of the measuring equipment used. Herein, "up to" a number (e.g., up to 50) includes the number (e.g., 50).

All numerical ranges are inclusive of their endpoints and nonintegral values between the endpoints unless otherwise stated (e.g., 1 to 5 includes 1, 1.5, 2, 2.75, 3, 3.80, 4, 5, etc.).

These and other aspects of the present disclosure will be apparent from the detailed description below. In no event, however, should the above summaries be construed as limitations on the claimed subject matter, which subject matter is defined solely by the attached claims, as may be amended during prosecution.

What is claimed is:

1. A self-mating fastener, comprising:
   a backing having a first side;
   a rail element protruding perpendicularly from, and extending in a longitudinal direction along, the first side of the backing, the rail element comprising:
     a base portion attached to the first side of the backing and having a base width; and
     a cap portion having a cap width that is greater than the base width, wherein the cap portion overhangs the base portion on opposing sides; and
   an electrically conductive contact element proximate to the rail element, wherein the contact element comprises:
     a first electrically conductive layer disposed on a portion of the cap portion; and
     a second electrically conductive layer on the first side of the backing adjacent to the base portion.

2. The self-mating fastener of claim 1, wherein the contact element extends perpendicularly from the first side of the backing and adjacent to the rail element, wherein the contact element is configured to provide resistive force in response to downward pressure from a distal end of the contact element toward the backing.

3. The self-mating fastener of claim 1, wherein the backing comprises multiple backing segments that are joined together, wherein the contact element extends perpendicularly from a first side of a first backing segment, and wherein the rail element extends perpendicularly from a first side of a second backing segment.

4. The self-mating fastener of claim 2, wherein the contact element further comprises a first base portion.

5. The self-mating fastener of claim 4, wherein the distal end of the contact element is not aligned with a first axis extending perpendicularly from the first base portion, and wherein the contact element forms an arc-shape having an inner surface and an outer surface that has a greater area than an area of the inner surface.

6. The self-mating fastener of claim 4, wherein the contact element further comprises a second base portion, wherein the first base portion and the second base portion extend from the backing to form a vertex, and wherein the contact element extends in a longitudinal direction along the backing and has a height from the backing to the vertex that is at least as high as a height of the base portion and is no greater than two times the height of the base portion.

7. The self-mating fastener of claim 6, wherein the first base portion and the second base portion each have an inner surface, wherein the inner surfaces of the first base portion and second base portion form a tube with the vertex in the longitudinal direction, and wherein the tube is filled with at least one of a medicament or a biological fluid.

8. The self-mating fastener of claim 1, wherein the backing has a second side, wherein the contact element comprises a third electrically conductive layer disposed on a portion of the second side in the longitudinal direction and aligned with the rail element, and wherein the self-mating fastener further comprises a conductive stake electrically coupling the first electrically conductive layer with the third electrically conductive layer.

9. The self-mating fastener of claim 1, wherein the backing is formed without through-holes.

10. A fastening system, comprising:
a first self-mating fastener according to claim 1; and
a second self-mating fastener according to claim 1, fastened to the first-self mating fastener such that the first self-mating fastener can slide relative to the second self-mating fastener
in a direction parallel to a length of the backing.

11. The fastening system of claim 10, wherein a first contact element of the first self-mating fastener and a second contact element of the second self-mating fastener are frictionally resistive toward each other, such that force is applied to the first contact element and the second contact element when the first self-mating fastener and second self-mating fastener slide relative to each other.

12. The fastening system of claim 10, wherein a first rail element of the first self-mating fastener is aligned with a second rail element of the second self-mating fastener, such that when fastened, a first cap portion of the first rail element engages with a second cap portion of the second rail element.

13. The fastening system of claim 10, a first contact element of the first self-mating fastener and a second contact element of the second self-mating fastener contact each other upon fastening of a first rail element of the first self-mating fastener with a second rail element of the second self-mating fastener to form an electrical connection.

14. The fastening system of claim 13, wherein the fastening system further comprises at least two conductive paths that are electrically insulated from each other.

15. The fastening system of claim 14, wherein at least one of the at least two conductive paths is formed between a second side of the first self-mating fastener and a second side of the second self-mating fastener.

16. An electronic system, comprising:
the fastening system of claim 10; and
a first electronic device,
wherein the first self-mating fastener is disposed on, and electrically coupled to, the first electronic device,
wherein the first electronic device is configured measure one or more physiological parameters,
wherein the second self-mating fastener is electrically coupled to the first electronic device through the first self-mating fastener,
wherein the first self-mating fastener is slidable along the second self-mating fastener while maintaining an electrical connection, and
wherein the second self-mating fastener is configured to attach to skin of a mammalian subject.

17. The electronic system of claim 16, further comprising:
a second electronic device; and
a third self-mating fastener electrically coupled to the second electronic device, wherein the third self-mating fastener is slidable with respect to the second self-mating fastener, and wherein the first electronic device is electrically coupled to the second electronic device via the second self-mating fastener.

18. The electronic system of claim 17, wherein the second self-mating fastener is configured to transport fluids from the first electronic device to the second electronic device.

19. The electronic system of claim 17, wherein at least one of the second electronic device or the second self-mating fastener is configured to fluidically couple to the skin of a patient to receive bodily fluids from the patient.

20. A self-mating fastener, comprising:
a backing having a first side;
a rail element protruding perpendicularly from, and extending in a longitudinal direction along, the first side of the backing, the rail element comprising:
a base portion attached to the first side of the backing and having a base width; and
a cap portion having a cap width that is greater than the base width, wherein the cap portion overhangs the base portion on opposing sides; and
an electrically conductive contact element extending perpendicularly from the first side of the backing and adjacent to the rail element, wherein the contact element is configured to provide resistive force in response to downward pressure from a distal end of the contact element toward the backing, and wherein the contact element comprises:
a first base portion; and
a second base portion,
wherein the first base portion and the second base portion extend from the backing to form a vertex, and
wherein the contact element extends in a longitudinal direction along the backing and has a height from the backing to the vertex that is at least as high as a height of the base portion and is no greater than two times the height of the base portion.

21. The self-mating fastener of claim 20, wherein the first base portion and the second base portion each have an inner surface, wherein the inner surfaces of the first base portion and second base portion form a tube with the vertex in the longitudinal direction, and wherein the tube is filled with at least one of a medicament or a biological fluid.

* * * * *